(12) United States Patent
Rodriguez

(10) Patent No.: US 6,909,008 B2
(45) Date of Patent: Jun. 21, 2005

(54) COCATALYST COMPOSITIONS

(75) Inventor: George Rodriguez, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 68 days.

(21) Appl. No.: 10/494,002

(22) PCT Filed: Oct. 29, 2002

(86) PCT No.: PCT/US02/34583
§ 371 (c)(1),
(2), (4) Date: Apr. 29, 2004

(87) PCT Pub. No.: WO03/040070
PCT Pub. Date: May 15, 2003

(65) Prior Publication Data
US 2004/0199021 A1 Oct. 7, 2004

Related U.S. Application Data
(60) Provisional application No. 60/336,103, filed on Nov. 2, 2001.

(51) Int. Cl.$^7$ .............................. C07F 7/02; C07F 5/02; B01J 31/00
(52) U.S. Cl. ............................ 556/9; 556/12; 556/173; 556/402; 502/103; 502/117; 502/154; 526/134; 526/163; 568/1
(58) Field of Search .............................. 556/9, 12, 173, 556/402; 568/1; 502/103, 117, 154; 526/134, 163

(56) References Cited

U.S. PATENT DOCUMENTS

| | | | | |
|---|---|---|---|---|
| 5,198,401 A | | 3/1993 | Turner et al. | 502/155 |
| 5,278,119 A | | 1/1994 | Turner et al. | 502/155 |
| 5,502,017 A | * | 3/1996 | Marks et al. | 502/103 |
| 5,869,723 A | * | 2/1999 | Hinokuma et al. | 556/402 |
| 2004/0110631 A1 | * | 6/2004 | Rodriguez | 502/103 |

FOREIGN PATENT DOCUMENTS

| | | | | |
|---|---|---|---|---|
| EP | 0 277 003 | 3/1988 | | C08F/4/64 |
| EP | 0 277 004 | 3/1988 | | C08F/4/64 |

OTHER PUBLICATIONS

Wrackmeyer et al., J. Organomet. Chem., vol. 562, No. 2, pp. 207–215 (1998).*
Imamoto et al., Tetrahedron Letters, Vo. 37, No. 4, pp. 503–504 (1996).*
Yamaguchi et al., Organic Letters, vol. 2, No. 26, pp. 4129–4132 (2000).*
Krivokapic et al., Advanced Materials, vol. 13, No. 9, pp. 652–656 (2001).*
Strauss, Steven. "The Search for Larger and More Weakly Coordinating Anions," Chem. Rev., vol. 93, pp. 927–942, (1993).
Quyoum et al., "A Carbocationic Olefin Polymerization Initiator Masquerading as a Ziegler–Natta Catalyst," J. Am. Chem. Soc., vol. 116, pp. 6435–6436, (1994).
Krivokapic et al., "Meso–Tetra–Alkynyl Porphyrins for Optical Limiting—A Survey of Group III and IV Metal Complexes," Advanced Materials, vol. 13, No. 9, pp. 652–656, (2001).
Hagelee et al., "The Influence of Silicon on the Formation of (Z/E)—Tetrasubstituted Ethylenes Via 1–Alkynylborates$^{2-}$", Syn. React. Inorg. Metal–Org. Chem., vol. 7(1), pp. 53–67 (1977).
Imamoto et al., "Synthesis and Properties of Trifluoromethanesulfonyloxy Derivatives of Tricyclohexylphosphine–Borane", Tetrahedron Letters, vol. 37, No. 4, pp. 503–504 (1996).
Wrackmeyer et al., "1,6–Dihydro–1,6–disilapentalene derivatives by 1,1–organoboration of triynes", Journal of Organometallic Chemistry, vol. 562, pp. 207–215, (1998).
Yamaguchi et al., "Tridurylboranes Extended by Three Arylethynyl Groups as a New Family of Boron–Based π–Electron Systems", Organic Letters, vol. 2, No. 26, pp. 4129–4132, (2000).

* cited by examiner

Primary Examiner—Porfirio Nazario-Gonzalez
(74) Attorney, Agent, or Firm—Catherine Bell

(57) ABSTRACT

An activator for olefin polymerization catalysts is disclosed. One aspect of the activator is that it comprises a group-13 central atom connected to at least one fluorinated aryl ring that is itself substituted with a silyl acetylenic group. Some embodiments employ a neutral activator and others employ the activator as an anion coupled with a ligand-abstracting cation. These activators are discrete molecules.

33 Claims, No Drawings

US 6,909,008 B2

COCATALYST COMPOSITIONS

CROSS REFERENCE TO RELATED APPLICATIONS

This application is a National Stage Application of International Application No. PCT/US02/34583, filed Oct. 29, 2002, which claims the benefit of Provisional Application No. 60/336,103, filed Nov. 2, 2001.

FIELD

This invention relates to polymerization cocatalyst compounds containing weakly coordinating Group-13-element anions and to the preparation of olefin polymers using ionic catalyst systems based on organometallic transition-metal cationic compounds stabilized by these anions.

BACKGROUND

The term "noncoordinating anion"(NCA) is now accepted terminology in the field of olefin and vinyl molecule, coordination, insertion, and carbocationic polymerization. See, for example, EP 0 277 003, EP 0 277 004, U.S. Pat. No. 5,198,401, U.S. Pat. No. 5,278,119, and Baird, Michael C., et al, *J. Am. Chem. Soc.* 1994, 116, 6435–6436. The noncoordinating anions are described to function as electronic stabilizing cocatalysts, or counterions, for essentially active, cationic metallocene polymerization catalysts. The term noncoordinating anion applies both to truly noncoordinating anions and to coordinating anions that are labile enough to undergo replacement by olefinically or acetylenically unsaturated molecules at the insertion site. These noncoordinating anions can be effectively introduced into a polymerization medium as Bronsted acid salts containing charge-balancing countercations, as ionic cocatalyst compounds, or mixed with an organometallic catalyst before adding it to the polymerization medium. See also, the review articles by S. H. Strauss, "The Search for Larger and More Weakly Coordinating Anions," *Chem. Rev.*, 93, 927–942 (1993).

U.S. Pat. No. 5,502,017, to Marks et al., addresses ionic metallocene polymerization catalysts for olefin polymerization containing a weakly coordinating anion comprising boron substituted with halogenated aryl substituents preferably containing silylalkyl substitution, such as a t-butyldimethyl-silyl substitution. Marks et al. disclose the weakly coordinating anion as the cocatalyst. The silylalkyl substitution is said to increase the solubility and thermal stability of the resulting metallocene salts. Examples 3–5 describe synthesis of and polymerization with the cocatalyst compound triphenylcarbenium tetrakis (4-dimethyl-t-butylsilyl-2, 3, 5, 6-tetrafluorophenyl) borate.

Leon A. Hagelee and Roland Köster published "Boron Compounds XLIV[1], The influence of silicon on the formation of (Z/E)-tetrasubstituted ethylenes via 1-alkynylborates; *Syn. React. Inorg. Metal-Org. Chem.*, 7(1), 53–67 (1977). This reference reports on NMR studies of borates that incorporate tri-methyl silyl groups.

Wrackmeyer, et al., published "1,6-Dihydro-1,6-disilapentalene derivatives by 1,1-organoboration of triynes". The triynes $R^1C\equiv\!-SiMe_2-C\equiv C-SiMe_2-C\equiv CR^1[R^1=H, SiMe_3, SnMe_3]$ were prepared, and their reactivity towards trior-ganoboranes $R_3B$ 6 [R=Et (a), $CH_2Ph$ (b), Ph c, 2-thienyl (d)] was studied. The products were characterised by their $^1H$-, $^{11}B$-, $^{13}C$-, $^{29}Si$- and $^{119}Sn$-NMR data.

Yamaguchi, et al., published "Tridurylboranes Extended by Three Arylethynyl Groups as a New Family of Boron-Based π-Electron Systems". A series of tris(phenylethynylduryl)boranes $(R-C_6H_4-C\equiv C-duryl)_3B$ with various substituents R have been prepared as air-stable solids owing to the steric protection of the boron atom by the three bulky duryl groups. These compounds show unique photophysical properties.

Imamoto, et al., published "Syntheses and Properties of Trifluoromethane-sulfonyloxy Derivatives of Tricyclohexylphosphine-Borane". Syntheses, structural characterizations, and reactions of tricyclohexylphosphine-trifluoromethanesulfonyloxyborane and tricyclohexylphosphine-bis(trifluoromethanesulfonyloxy)-borane are described.

In view of the above, there is a continuing need for olefin polymerization activators both to improve the industrial economics of solution polymerization and to provide alternative activating compounds for ionic, olefin polymerization catalyst systems.

SUMMARY

The invention provides cocatalyst compounds that can be combined with catalyst precursor compounds to form active catalysts for olefin insertion, coordination, or carbocationic polymerization, as well as catalyst systems containing such cocatalyst compounds. (For purposes of this document, "cocatalyst compound" is interchangeable with "cocatalyst activator compound" and "activator"). Olefin polymerization can proceed by catalyst formation followed by, or in situ catalyst formation essentially concurrent with, contacting the catalyst with appropriate molecules: those having accessible, olefinic or acetylenic unsaturation or having olefinic unsaturation capable of cationic polymerization. More generally, an appropriate olefin is one that is polymerizable by a catalyst system that uses the invention cocatalyst compounds. The catalysts according to the invention are suitable for preparing polymers and copolymers from olefinically and acetylenically unsaturated molecules.

Some invention embodiments select the cocatalyst to be neutral with three fluoroaryl ligands, while others select the cocatalyst to be ionic with four fluoroaryl ligands. Some embodiments select the aryl ligand (otherwise known as a ring assembly) so that it comprises at least one fluorine group.

When neutral, the cocatalyst comprises a Group-13 element bound to fluoroaryl ligands in which at least one fluoroaryl ligand is substituted with at least one acetylenic group: (BULKY-CC-). BULKY represents a group that is bulky enough to kinetically or thermodynamically impede reaction of the acetlylenic group with the activated metallocene catalyst. The neutral cocatalyst is itself the ligand abstracting moiety. Upon catalyst activation, the neutral cocatalyst becomes an NCA. In more specific embodiments, at lest one aryl ligand is substituted with at least one fluorine atom (i.e. fluoro substituted).

When ionic, the cocatalyst contains a cationic, ligand-abstracting moiety (an activating cation) and an NCA moiety comprising a Group-13 element bound to aryl ligands in which at least one aryl ligand is substituted with at least one acetylenic group: (BULKY-CC-).

Some embodiments select a triisopropylsilylacetylenic substitution on each aryl ligand. Some embodiments select the Group-13 element to be boron. Some embodiments select the aryl ligands so that, other than acetylenic groups, the aryl ligand or ring assembly is perfluorinated.

The ligand-abstracting moiety can abstract an alkyl group from, or break a carbon-metal bond in, an organometallic compound (i.e., the catalyst precursor) upon contact with that compound. This process leaves a cationic catalyst, a neutral compound, and an NCA.

This invention relates to a composition of matter that contains an anionic central core wherein the anionic central core comprises a Group-13 atom. This group-13 atom is connected to four ring assemblies wherein at least one ring assembly comprises an acetylene moiety.

This invention also relates to a composition of matter that contains a nuetral central core comprising a Group-13 atom. This atom is connected to three ring assemblies wherein at least one ring assembly comprises an acetylene moiety.

In addition, this invention relates to methods for using these compositions and to products produced using them.

DETAILED DESCRIPTION

Catalyst system encompasses a catalyst precursor/activator pair. When catalyst system is used to describe such a pair before activation, it means the un-activated catalyst together with the activator. When catalyst system is used to describe such a pair after activation, it means the activated catalyst and the NCA or other charge-balancing moiety. In some cases, catalyst refers to the activated catalyst.

One aspect of this invention is an NCA comprising an acetylene substituent, as shown in the following formula.

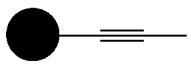

The filled circle represents a bulky group that is large enough to impede or slow down access by the active site of the metallocene to the olefinic unsaturation of the acetylenic group. A more specific representation is shown below.

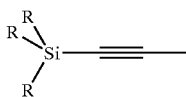

In this representation, $R_3Si$ represents the bulky group. Thus, the acetylene substitution comprises a bulky group and an acetylenic group. Si is silicon. Each R is an organic radical and can be the same or different. At least one R is selected from methyl, ethyl, n-propyl, i-propyl, n-butyl, s-butyl, t-butyl, 1-pentyl, 1-methylbut-1-yl, 2-methylbut-1-yl, 3-methylbut-1-yl, 2-pentyl, 3-pentyl, 1,1-dimethylprop-1-yl, 1,2-dimethylprop-1-yl, and 2,2-dimethylprop-1-yl. As with the isomers of the propyl, butyl, and pentyl radicals, R can also be selected from the isomers of the hexyl, heptyl, and octyl radicals. Exemplary silyl groups include the following Octadecyldimethylsilyl, (3-cyanopropyl)dimethylsilyl, (pentafluorophenyl)dimethylsilyl, (3-chloropropyl)dimethylsilyl, allyldimethylsilyl, butyldimethylsilyl, (chloromethyl)dimethylsil, decyldimethyl-silyl, diisopropylsilyl, diisopropyloctylsilyl, dimethyl(3,3,3-trifluoropropyl)silyl, dimethyl(3,3,4,4,5,5,6,6,6-nonafluorohexyl)silyl, dimethyldodecylsilyl, dimethylisopropylsilyl, dimethylphenylsilyl, dimethyl-propyl-silyl, dimethyl-thexylsilyl, diphenyl-methylsilyl, methyl-phenyl-silyl, methyl-phenyl-vinylsilyl, Octadecyldimethylsilyl, octyldimethylsilyl, tert-butyldimethylsilyl, tert-butyldiphenylsilyl, tribenzylsilyl, triethylsilyl, triisopropylsilyl, trimethylsilyl, triphenylsilyl, vinyldimethylsilyl, and dimethyl-thexylsilyl. Whatever the actual selection of the trialkyl silyl group it must function as a bulky group. Alternatively, suitable bulky groups need not contain silicon. And they need not contain carbon.

To define nomenclature, the structure of the 2-pentyl radical is shown below. This radical can also be called the 1-methylbut-1-yl radical. The connection to Si is shown.

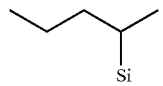

The isopropylsilylacetylenic group has the formula shown below. It can be more formally called the 2-(triisopropylsilyl)ethynyl or ethyn-1-yl radical.

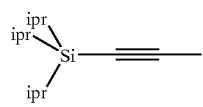

One aspect of this invention is an NCA comprising the acetylenic groups discussed above connected to an aryl group. The resulting assembly then ligates or connects to a Group-13 element (Group-13 elements are sometimes referred to as triels and abbreviated as Tr). Some embodiments select the triel or Group-13 element to be B or Al. Some embodiments select the aryl group to be fluorinated or perfluorinated. Several exemplary NCAs are shown below.

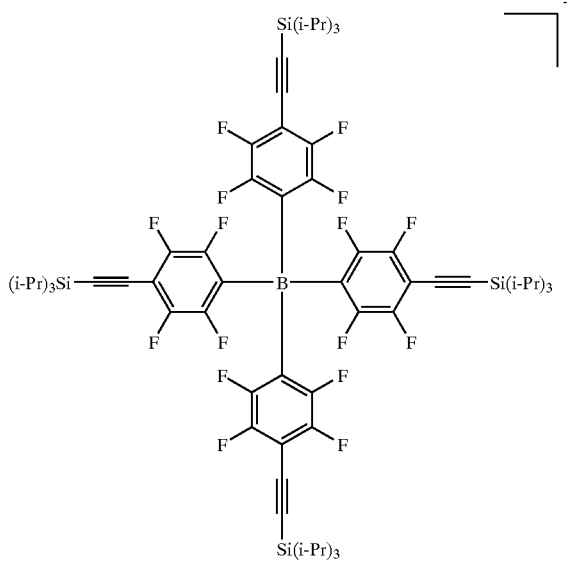

tetrakis{para-[2-(triisopropylsilyl)acetyl]tetrafluorophenyl}borate, for purposes of this disclosure, the previous term is interchangeable with tetrakis{4-[2-(triisopropylsilyl)ethynyl]tetrafluorophenyl}borate

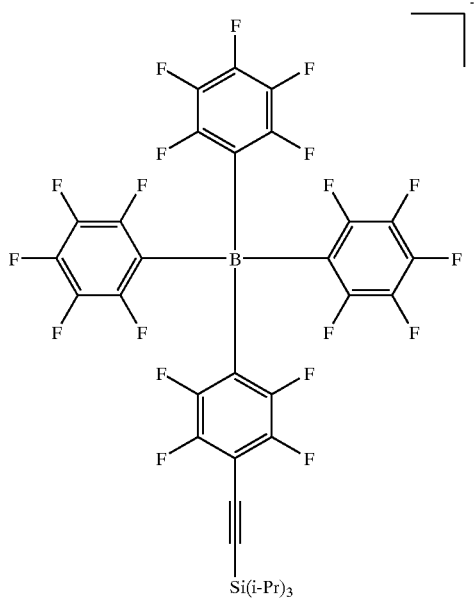

tris {pentafluorophenyl}{para-[2-(triisopropylsilyl) acetyl]} tetrafluoro-phenyl}borate. For purposes of this disclosure, the previous term is interchangeable with tris {pentafluorophenyl}{4-[2-(triisopropylsilyl)ethynyl]-tetrafluorophenyl}borate.

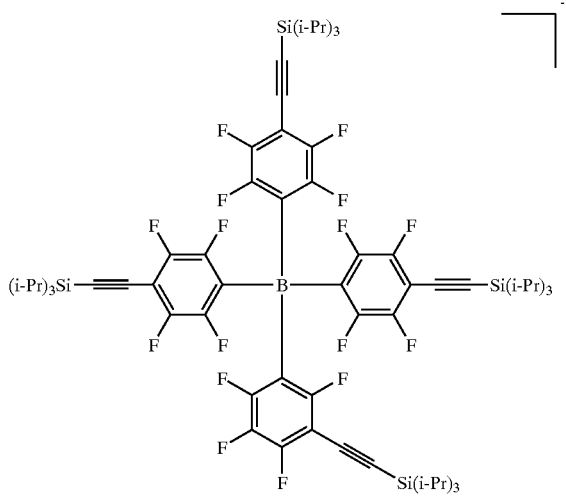

tris{4-[2-(triisopropylsilyl)ethynyl]tetrafluorophenyl}{3-[2-(triisopropylsilyl)ethynyl]tetrafluorophenyl}borate The NCAs as shown above have the ethynic or acetylenic portion of the acetylenic group directly connected to the fluoroaryl ligand.

The ligands around the Group-13 atom serve to stabilize the ion's charge. Furthermore, the ligands control the degree of contact between the catalyst and cocatalyst. With appropriate NCA, these two effects combine to diminish the ionic attraction between the catalyst and cocatalyst. Alternatively, the NCA can be an assembly in which the anionic charge spreads out over the molecule making the charge more diffuse. After catalyst activation, the cocatalyst should either be completely non-coordinating or coordinate weakly enough so that the anion does not substantially impede the monomer's access to the catalyst.

Phenyl, biphenyl, naphthyl, indenyl, anthracyl, fluorenyl, azulenyl, phenanthrenyl, and pyrenyl are suitable aryl radicals. Some embodiments select phenyl, biphenyl, or naphthyl as the aryl radicals. Exemplary ArF ligands and ArF substituents useful in this invention specifically include the fluorinated species of these aryl radicals. Perfluorinated aryl groups also function and include substituted ArF groups having substituents in addition to fluorine, such as fluorinated hydrocarbyl groups. The disclosures of U.S. Pat. Nos. 5,198,401, 5,296,433, 5,278,119, 5,447,895, 5,688,634, 5,895,771, WO 93/02099, WO 97/29845, WO 99/43717, WO 99/42467 and copending U.S. application Ser. No. 09/261,627, filed 3 Mar. 1999, and its equivalent WO 99/45042 teach suitable ArF groups. Some embodiments replace at least one-third of the hydrogen atoms connected to aromatic ligands with fluorine; some embodiments select perfluorinated aryl ligands. Perfluorinated means that each aryl hydrogen atom is substituted with fluorine or fluorcarbyl substituents, e.g., trifluoromethyl, pentafluoroethyl, heptafluoro-isopropyl, tris(trifluoromethyl) silyltetrafluoroethyl, and bis(trifluoroethyl) (heptafluoropropyl)silyltetrafluoroethyl.

The goal of fluorination is to remove abstractable hydrogen from the NCA. Therefore, any ligand choice or substitution pattern that minimizes the number of abstractable hydrogen is useful in this invention's practice. Thus, suitable ligand choices and substitution patterns will depend somewhat on the selected catalyst. Not all hydrogen substituents must be fluorine-replaced as long as the remaining hydrogen substituents are substantially non-abstractable by the specific catalyst of the catalyst system. Substantially non-abstractable means that the hydrogen may be extractable but at levels low enough so that the degree of chain termination and catalyst poisoning remains below that which is commercially reasonable. Some embodiments target lesser levels of abstractability. Cocatalyst activators can effectively activate catalysts for solution, bulk, slurry, and gas phase polymerization processes.

Cation counterparts for invention noncoordinating anion salts include those known in the art for NCAs. Various cation classes include nitrogen-containing cations such as in the anilinium and ammonium salts of U.S. Pat. No. 5,198,401 and WO 97/35893; the carbenium, oxonium, or sulfonium cations of U.S. Pat. No. 5,387,568; metal cations, e.g., $Ag^+$; the silylium cations of WO 96/08519; and those of the hydrated, Group-1 or -2 metal cations of WO 97/22635.

Additionally, invention NCAs can come from neutral Lewis acids comprising a Group-13 metal or metalloid center and from one to three halogenated aryl ligands as described above for the invention. Complementary ligands are selected from those known in the art for noncoordinating anions. Thus some co-catalyst embodiments are neutral and become anionic during the activation process. Two such examples are shown below.

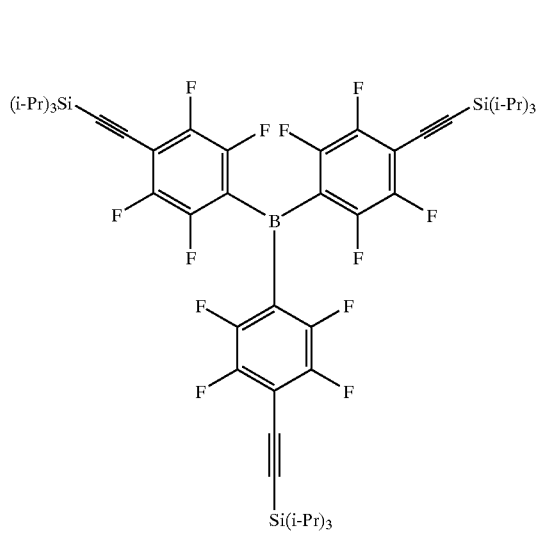

tris{para-[2-(triisopropylsilyl)acetyl]-tetrafluorophenyl}borane or tris {4-[2-(triisopropylsilyl)ethynyl]tetrafluorophenyl}borane

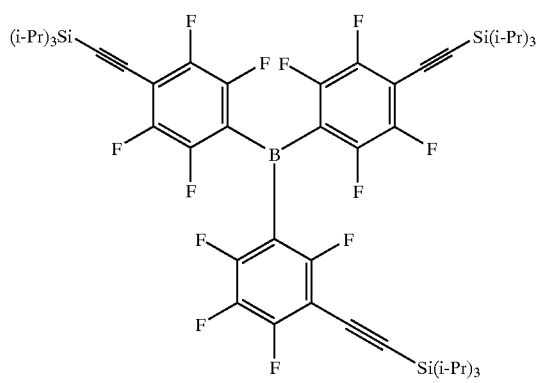

bis{4-[2-(triisopropylsilyl)ethynyl]tetrafluorophenyl} {3-[2-(triisopropylsilyl)ethynyl)tetrafluorophenyl}borane

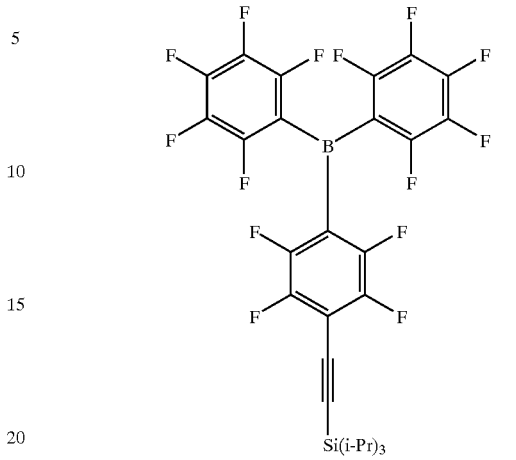

bis{pentafluorophenyl} {para-[2-(triisopropylsilyl)acetyl])}tetrafluorhenyl)borane or bis{pentafluorophenyl} {4-[2-(triisopropylsilyl) ethynyltetrafluorophenyl}borane In operation, an anionic cocatalyst reacts with the catalyst precursor leaving an activated cationic catalyst and a weakly coordinating anion. Before activation, the cocatalyst contains a cation. Activation occurs when that cation either abstracts a hydride, alkyl, or substituted alkyl ligand, Q, from the catalyst precursor or cleaves a metal-organic bond in the precursor.

Activation transforms the cation of the cocatalyst into a neutral molecule; the non-coordinating anion remains anionic. Activation also transforms the neutral catalyst precursor into a cationic catalyst, typically by abstracting a hydride or anionic alkyl, which combines with the proton from the cocatalyst.

The acetylenic-substituted activators or cocatalysts may be prepared as follows.

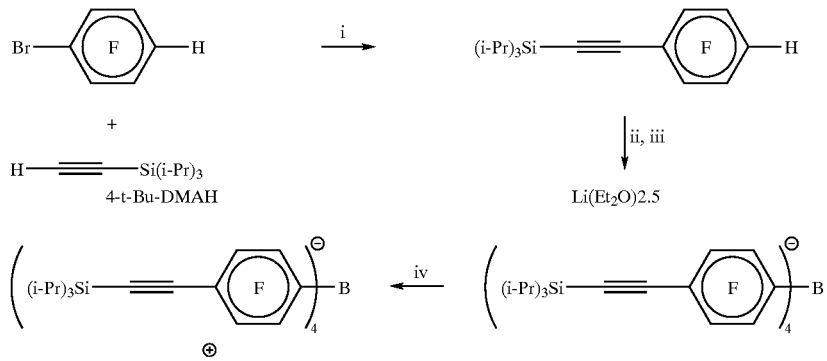

i. Sonogashira conditions, ii BuLi, −78 deg C., diethylether as solvent. iii ¼ BCl$_3$. iv. 4-tBu-DMAHCl, methylene chloride as solvent, 25 deg C.

Catalyst Precursor Compounds

When neutral cocatalysts are employed, the activation process is believed to proceed somewhat differently. The neutral cocatalyst itself abstracts a ligand from the catalyst precursor becoming anionic in the process. After activation, the activated cationic catalyst is charged balanced by the NCA. In the case of a neutral cocatalyst, the NCA is frequently the reaction product of the cocatalyst and the abstracted ligand.

Suitable catalyst precursor compounds for use in this invention include the known organometallic, transition metal compounds useful for traditional Ziegler-Natta polymerization, particularly the metallocenes known to be useful in polymerization. The catalyst precursor must be susceptible to activation by invention cocatalysts. Useful catalyst precursors include Group-3–10 transition metal compounds in which at least one metal ligand can be abstracted by the cocatalyst. Particularly, those abstractable ligands include hydride, hydrocarbyl, hydrocarbylsilyl, and their lower-alkyl-substituted ($C_1$–$C_{10}$) derivatives. Examples include hydride, methyl, benzyl, dimethylbutadiene, etc. Abstractable ligands and transition metal compounds comprising them include those metallocenes described in, for example, U.S. Pat. No. 5,198,401 and WO 92/00333. Syntheses of these compounds are well known from the published literature. Additionally, in those cases where the metal ligands include labile halogen, amido, or alkoxy ligands (for example, biscyclopentadienyl zirconium dichloride), which may not allow for ready abstraction by invention's cocatalysts, the ligands can be replaced with abstractable ones. This replacement uses known routes such as alkylation with lithium or aluminum hydrides, alkyls, alkylalumoxanes, Grignard reagents, etc. See also EP 0 500 944 and EP 0 570 982 for the reaction of organoaluminum compounds with dihalo-substituted metallocenes prior to catalyst activation.

Additional descriptions of metallocene compounds with, or that can be alkylated to contain, at least one ligand abstractable to form catalytically active transition-metal cations appear in the patent literature. (E.g., EP-A-0 129 368, U.S. Pat. Nos. 4,871,705, 4,937,299, 5,324,800, 5,470,993, 5,491,246, 5,512,693, EP-A-0 418 044, EP-A-0 591 756, WO-A-92/00333, WO-A-94/01471 and WO 97/22635.) Such metallocenes can be described as mono- or biscyclopentadienyl-substituted Group-3, -4, -5, or -6 transition metals. The transition metal ligands may themselves be substituted with one or more groups, and the ligands may bridge to each other or bridge through a heteroatom to the transition metal. The size and constituency of the ligands and bridging elements should be chosen in the literature-described manner to enhance activity and to select desired characteristics. Embodiments in which the cyclopentadienyl rings (including substituted, cyclopentadienyl-based, fused-ring systems, such as indenyl, fluorenyl, azulenyl, or their substituted analogs), when bridged to each other, are lower-alkyl substituted ($C_1$–$C_6$) in the 2 position (with or without a similar 4-position substituent in the fused ring are useful). The cyclopentadienyl rings may additionally comprise alkyl, cycloalkyl, aryl, alkylaryl, and arylalkyl substituents, the latter as linear, branched, or cyclic structures including multi-ring structures, for example, those of U.S. Pat. Nos. 5,278,264 and 5,304,614. In some embodiments, such substituents should each have essentially hydrocarbyl characteristics and will typically contain up to 30 carbon atoms, but may contain heteroatoms, such as 1 to 5 non-hydrogen or non-carbon atoms, e.g., N, S, O, P, Ge, B and Si.

Invention activators are useful with essentially all known metallocene catalyst that are suitable for preparing polyolefins from $C_2$–$C_{10}$ α-olefin monomer or mixtures of monomers, see again WO-A-92/00333 and U.S. Pat. Nos. 5,001,205, 5,198,401, 5,324,800, 5,304,614 and 5,308,816, for specific listings. Criteria for selecting suitable metallocene catalysts for making polyethylene and polypropylene are well known in the art, in both patent and academic literature, see for example *Journal of Organometallic Chemistry* 369, 359–370 (1989). Likewise, methods for preparing these metallocenes are also known. Typically, the catalysts are stereorigid, asymmetric, chiral, or bridged-chiral metallocenes. See, for example, U.S. Pat. No. 4,892,851, U.S. Pat. No. 5,017,714, U.S. Pat. No. 5,296,434, U.S. Pat. No. 5,278,264, WO-A-(PCT/US92/10066) WO-A-93/19103, EP-A2-0 577 581, EP-A1-0 578 838, and academic literature "The Influence of Aromatic Substituents on the Polymerization Behavior of Bridged Zirconocene Catalysts", Spaleck, W., et al, *Organometallics* 1994, 13, 954–963, and "ansa-Zirconocene Polymerization Catalysts with Annelated Ring Ligands-Effects on Catalytic Activity and Polymer Chain Lengths", Brinzinger, H., et al, Organometallics 1994, 13, 964–970, and documents referred to therein. Though many of these references deal with alumoxane-activated catalyst systems, analogous metallocenes can be activated with this invention's cocatalysts. In catalyst systems lacking abstractable ligands, at least one non-abstractable ligand must first be replaced with an abstractable one. Replacement by alkylation, as described above, is one example.

Additionally, the metallocenes should contain a group into which an ethylene or α-olefin group, —C=C—, may insert, for example, hydride, alkyl, alkenyl, or silyl. See additional description in G. G. Hlatky, "Metallocene catalysts for olefin polymerization Annual review of 1996", Coordination Chemistry Reviews, 181, 243–296 (Elsevier Science, 1999).

Representative metallocene compounds can have the formula:

where M is a Group-3–10 metal; $L_A$ is a substituted or unsubstituted, cyclopentadienyl or heterocyclopentadienyl ligand connected to M; and $L_B$ is a ligand as defined for $L_A$, or is J, a heteroatom ligand connected to M. $L_A$ and $L_B$ may connect to each other through a Group-13–16-element-containing bridge. $L_{Ci}$ is an optional, neutral, non-oxidizing ligand connected to M (i equals 0 to 3); and D and E are the same or different labile ligands, optionally bridged to each other, $L_A$, or $L_B$. Each of D and E are connected to M. Some embodiments select M to be a member of the Group-3–6 transition metals. Other embodiments select M to be a Group-4 transition metal. Some embodiments select M to be Ti, Zr, or Hf.

D and E's identity is functionally constrained. The first constraint is that upon activation, either the D-M or the E-M connection must break. D and E should be chosen to facilitate this. Another constraint is that a polymerizable molecule must be able to insert between M and whichever of D or E remains.

Cyclopentadienyl and heterocyclopentadienyl ligands encompass fused-ring systems including but not limited to indenyl and fluorenyl radicals. Also, the use of heteroatom-containing rings or fused rings, where a non-carbon, Group-13, -14, -15, or -16 atom replaces a ring carbon is within the term "cyclopentadienyl" for this specification. See, for example, the background and illustrations of WO 98/37106, having priority with U.S. Ser. No. 08/999,214, filed Dec. 29, 1997, and WO 98/41530, having priority with U.S. Ser. No. 09/042,378, filed Mar. 13, 1998. Substituted cyclopentadienyl structures are structures in which one or more hydrogen atoms are replaced by a hydrocarbyl, hydrocarbylsilyl, or similar heteroatom-containing structure. Hydrocarbyl structures specifically include $C_{1-C30}$ linear, branched, and cyclic alkyl, and aromatic fused and pendant rings. These rings may also be substituted with ring structures.

Catalyst precursors also include the mono- and biscyclopentadienyl compounds such as those listed and described in U.S. Pat. Nos. 5,017,714, 5,324,800, WO 92/00333 and EP-A-0 591 756.

Bis amide catalyst precursors are useful with invention cocatalysts. Bisamide catalyst precursors are those precursors that have the following formula:

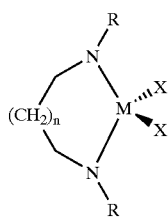

M is Ti, Zr, or Hf. R are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the bisamide catalyst precursor must first be chemically modified to transform X into an abstractable ligand. This can be done by alkylation, for example.

Pyridine bisamide catalyst precursors are also useful with invention cocatalysts. Pyridine bisamide catalyst precursors are those precursors that have the following formula:

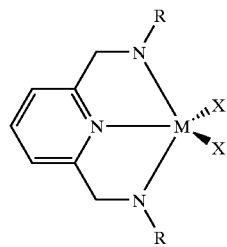

M is Ti, Zr, or Hf. R are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the pyridine bisamide catalyst precursor must first be chemically modified to transform X into an abstractable ligand. This can be done by alkylation, for example.

Amine bisamide catalyst precursors are also useful with invention cocatalysts. Amine bisamide catalyst precursors are those precursors that have the following formula:

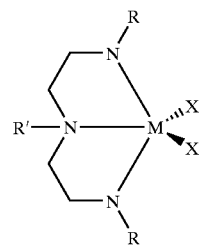

M is Ti, Zr, or Hf. R and $R^1$ are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the amine bisamide catalyst precursor must first be chemically modified to transform X into an abstractable ligand. This can be done by alkylation, for example.

Additional exemplary metallocene-type catalysts include those metallocene compounds represented by the formula:

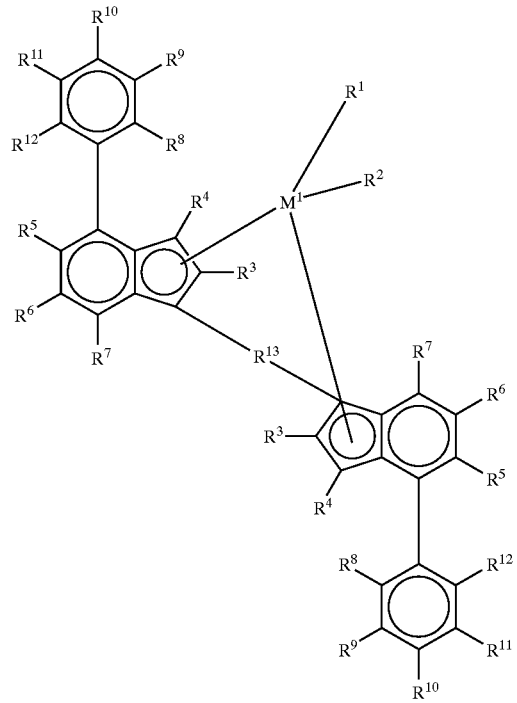

In the above structure, $M^1$ is selected from titanium, zirconium, hafnium, vanadium, niobium, tantalum, chromium, molybdenum, or tungsten.

$R^1$ and $R^2$ are identical or different and are selected from hydrogen atoms, $C_1$–$C_{10}$ alkyl groups, $C_1$–$C_{10}$ alkoxy groups, $C_6$–$C_{10}$ aryl groups, $C_6$–$C_{10}$ aryloxy groups, $C_2$–$C_{10}$ alkenyl groups, $C_2$–$C_{40}$ alkenyl groups, $C_7$–$C_{40}$ arylalkyl groups, $C_7$–$C_{40}$ alkylaryl groups, $C_8$–$C_{40}$ arylalkenyl groups, OH groups or halogen atoms; or conjugated dienes that are optionally substituted with one or more hydrocarbyl, tri(hydrocarbyl)silyl groups or hydrocarbyl, tri(hydrocarbyl) silylhydrocarbyl groups. The conjugated diene can contain up to 30 atoms not counting hydrogen.

$R^3$ are the same or different and are selected from hydrogen atom, halogen atoms, $C_1$–$C_{10}$ halogenated or unhalogenated alkyl groups, $C_6$–$C_{10}$ halogenated or unhalogenated aryl groups, $C_2$–$C_{10}$ halogenated or unhalogenated alkenyl groups, $C_7-C_{40}$ halogenated or unhalogenated arylalkyl groups, $C_7-C_{40}$ halogenated or unhalogenated alkylaryl groups, $C_8-C_{40}$ halogenated or unhalogenated arylalkenyl groups, $-NR_{12}$, $-SR'$, $-OR'$, $-OSiR'_3$ or $-PR'_2$ radicals in which R is one of a halogen atom, a $C_1-C_{10}$ alkyl group, or a $C_6-C_{10}$ aryl group.

$R^4$ to $R^7$ are the same or different and are hydrogen, as defined for $R^3$ or two or more adjacent radicals $R^5$ to $R^7$ together with the atoms connecting them form one or more rings.

$R^{13}$ is selected from

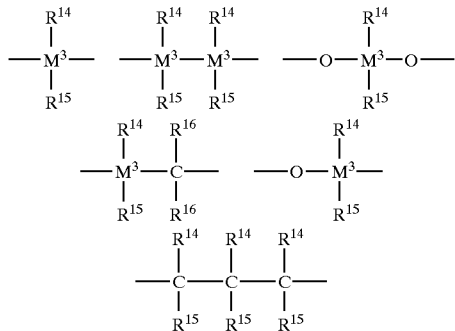

$-B(R^{16})-$, $-Al(R^{14})-$, $-Ge-$, $-Sn-$, $-O-$, $-S-$, $-SO-$, $-SO_2-$, $-N(R^{14})-$, $-CO-$, $-P(R^{14})-$ $-P(O)(R^{14})-$, $B(NR^{14}R^{15})-$ and $-B[N(SiR^{14}R^{15}R^{16})_2]-$, $R^{14}$, $R^{15}$ and $R^{16}$ are each independently selected from hydrogen, halogen, $C_1-C_{20}$ alkyl groups, $C_6-C_{30}$ aryl groups, $C_1-C_{20}$ alkoxy groups, $C_2-C_{20}$ alkenyl groups, $C_7-C_{40}$ arylalkyl groups, $C_8-C_{40}$ arylalkenyl groups and $C_7-C_{40}$ alkylaryl groups, or $R^{14}$ and $R^{15}$, together with the atom(s) connecting them, form a ring; and $M^3$ is selected from carbon, silicon, germanium and tin. Alternatively, $R^{13}$ is represented by the formula:

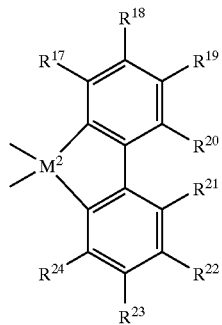

wherein $R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings; $M^2$ is carbon, silicon, germanium, or tin.

$R^8$, $R^9$. $R^{10}$ $R^{11}$ and $R^{12}$ are identical or different and have the meanings stated for $R^4$ to $R^7$.

Non-limiting representative catalyst precursor compounds include the following compounds: pentamethylcyclopentadienyltitanium isopropoxide; pentamethylcyclopentadienyltribenzyl titanium; dimethylsilyltetramethylcyclopentadienyl-t-butylamido titanium dichloride; pentamethylcyclopentadienyl titanium trimethyl; dimethylsilyltetramethylcyclopentadienyl-t-butylamido zirconium dimethyl; dimethylsilyltetramethylcyclopentadienyl-dodecylamido hafnium dihydride; dimethylsilyltetramethylcyclopentadienyl-dodecylamido hafnium dimethyl; unbridged biscyclopentadienyl compounds such as bis(1-methyl; 3-butylcyclopentadienyl) zirconium dimethyl; (pentamethylcyclopentadienyl-cyclopentadienyl)zirconium dimethyl; (tetramethylcyclopentadienyl)(n-propylcyclopentadienyl) zirconium dimethyl; bridged bis-cyclopentadienyl; dimethylsilylbis-(tetrahydroindenyl)zirconium dichloride; silacyclobutyl(tetramethylcyclopentadienyl) (n-propyl-cyclopentadienyl)zirconium dimethyl; dimethylsilyl (bisindenyl)zirconium dichloride; dimethylsily(bisindenyl) hafnium dimethyl; dimethylsilylbis(2-methylbenzindenyl) zirconium dichloride; dimethylsilylbis(2-methylbenzindenyl)zirconium dimethyl; and fluorenyl-ligand-containing compounds; e.g.; diphenylmethyl (fluorenyl)(cyclopentadienyl)zirconium dimethyl; tetrabenzyl zirconium; tetrabis(trimethyl-silylmethyl) zirconium; oxotris(trimethlsilylmethyl)-vanadium; tetrabenzyl hafnium; tetrabenzyl titanium; bis (hexamethyldisilazido)-dimethyltitanium; tris (trimethylsilylmethyl)niobium dichloride; tris (trimethylsilylmethyl)tantalum dichloride; (benzylcyclopentadienyl)(cyclopentadienyl)-hafnium dihydride; (benzylcyclopentadienyl)(cyclopentadienyl)hafnium dimethyl; (benzylcyclopentadienyl)(cyclopentadienyl) titanium dihydride; (benzylcyclopentadienyl) (cyclopentadienyl)titanium dimethyl; (benzylcyclopentadienyl)-(cyclopentadienyl)zirconium dihydride; (benzylcyclopentadienyl)(cyclopentadienyl)zirconium dimethyl; (cyclohexylmethylcyclopentadienyl) (cyclopentadienyl)hafnium dimethyl; (cyclohexylmethylcyclopentadienyl)(cyclopentadienyl)-titanium dimethyl; (cyclohexylmethylcyclopentadienyl)(cyclopentadienyl)-zirconium dimethyl; (cyclohexylmethylcyclopentadienyl) (cyclopentadienyl)-hafnium dihydride; (cyclohexylmethyl-cyclopentadienyl)(cyclopentadienyl)-titanium dihydride; (cyclohexylmethylcyclopentadienyl)(cyclopentadienyl)-zirconium dihydride; (dimethylcyclopentadienyl) (cyclopentadienyl)hafnium dihydride; (dimethylcyclopentadienyl)(cyclopentadienyl)hafnium dimethyl; (dimethyl-cyclopentadienyl)(cyclopentadienyl)titanium dihydride; (dimethylcyclopentadienyl)(cyclopentadienyl) titanium dimethyl; (dimethylcyclopentadienyl) (cyclopentadienyl)zirconium dihydride; (dimethylcyclopentadienyl)(cyclopentadienyl)-zirconium dimethyl; (diphenylmethylcyclopentadienyl)(cyclopentadienyl) hafnium dimethyl; (diphenylmethylcyclopentadienyl) (cyclopentadienyl)titanium dimethyl; (diphenylmethyl-cyclopentadienyl)(cyclopentadienyl)zirconium dimethyl; (diphenylmethylcyclopentadienyl)(cyclopentadienyl) hafnium dihydride; (diphenylmethylcyclopentadienyl) (cyclopentadienyl)titanium dihydride; (diphenylmethyl-cyclopentadienyl)(cyclopentadienyl)zirconium dihydride; (ethylcyclopentadienyl)(cyclopentadienyl)hafnium dimethyl; (ethylcyclopentadienyl)(cyclopentadienyl)titanium dimethyl; (ethylcyclopentadienyl)(cyclopentadienyl) zirconium dimethyl; (ethylcyclopentadienyl) (cyclopentadienyl)hafnium dihydride; (ethylcyclopentadienyl)(cyclopentadienyl)titanium dihydride; (ethylcyclopentadienyl)-(cyclopentadienyl)zirconium dihydride; (ethyltetramethylcyclopentadienyl) (cyclopentadienyl)hafnium dihydride; (ethyltetramethyl-cyclopentadienyl)(cyclopentadienyl)hafnium dimethyl; (ethyltetramethylcyclopentadienyl)(cyclopentadienyl)-titanium dihydride; (ethyltetramethylcyclopentadienyl) (cyclopentadienyl)titanium dimethyl; (ethyltetramethyl-cyclopentadienyl)(cyclopentadienyl)zirconium dihydride; (ethyltetramethylcyclopentadienyl)(cyclopentadienyl)

zirconium dimethyl; (indenyl)(cyclopentadienyl)hafnium dihydride; (indenyl)(cyclopentadienyl)-hafnium dimethyl; (indenyl)(cyclopentadienyl)titanium dihydride; (indenyl)-(cyclopentadienyl)titanium dimethyl; (indenyl)(cyclopentadienyl)zirconium dihydride; (indenyl)(cyclopentadienyl)zirconium dimethyl; (methylcyclopentadienyl)-(cyclopentadienyl)hafnium dihydride; (methylcyclopentadienyl)(cyclopentadienyl)hafnium dimethyl; (methylcyclopentadienyl)(cyclopentadienyl)titanium dihydride; (methylcyclopentadienyl)(cyclopentadienyl)titanium dimethyl; (methylcyclopentadienyl)(cyclopentadienyl)zirconium dihydride; (methylcyclopentadienyl)(cyclopentadienyl)zirconium dimethyl; (n-butylcyclopentadienyl)(cyclopentadienyl)hafnium dimethyl; (n-butylcyclopentadienyl)(cyclopentadienyl)-titanium dimethyl; (n-butylcyclopentadienyl)(cyclopentadienyl)zirconium dimethyl; (n-butylcyclopentadienyl)(cyclopentadienyl)hafnium dihydride; (n-butylcyclopentadienyl)(cyclopentadienyl)titanium dihydride; (n-butylcyclopentadienyl)(cyclopentadienyl)zirconium dihydride; (pentamethylcyclopentadienyl)-(cyclopentadienyl)hafnium dihydride; (pentamethylcyclopentadienyl)(cyclopentadienyl)hafnium dimethyl; (pentamethylcyclopentadienyl)(cyclopentadienyl)-titanium dihydride; (pentamethylcyclopentadienyl)(cyclopentadienyl)titanium dimethyl; (pentamethylcyclopentadienyl)(cyclopentadienyl)zirconium dihydride; (pentamethylcyclopentadienyl)(cyclopentadienyl)zirconium dimethyl; (propylcyclopentadienyl)(cyclopentadienyl)hafnium dimethyl; (propylcyclopentadienyl)-(cyclopentadienyl)titanium dimethyl; (propylcyclopentadienyl)(cyclopentadienyl)-zirconium dimethyl; (propylcyclopentadienyl)(cyclopentadienyl)hafnium dihydride; (propylcyclopentadienyl)(cyclopentadienyl)titanium dihydride; (propylcyclopentadienyl)(cyclopentadienyl)zirconium dihydride; (t-butylcyclopentadienyl)-(cyclopentadienyl)hafnium dimethyl; (t-butylcyclopentadienyl)(cyclopentadienyl)titanium dimethyl; (t-butylcyclopentadienyl)(cyclopentadienyl)zirconium dimethyl; (t-butylcyclopentadienyl)(cyclopentadienyl)hafnium dihydride; (t-butylcyclopentadienyl)(cyclopentadienyl)titanium dihydride; (t-butylcyclopentadienyl)(cyclopentadienyl)zirconium dihydride; (tetramethylcyclopentadienyl)(cyclopentadienyl)hafnium dihydride; (tetramethylcyclopentadienyl)-(cyclopentadienyl)hafnium dimethyl; (tetramethylcyclopentadienyl)(cyclopentadienyl)titanium dihydride; (tetramethylcyclopentadienyl)(cyclopentadienyl)-titanium dimethyl; (tetramethylcyclopentadienyl)(cyclopentadienyl)zirconium dihydride; (tetramethylcyclopentadienyl)(cyclopentadienyl)zirconium dimethyl; (trifluoromethylcyclopentadienyl)(cyclopentadienyl)hafnium dihydride; (trifluoromethyl-cyclopentadienyl)(cyclopentadienyl)titanium dihydride; (trifluoromethylcyclopentadienyl)(cyclopentadienyl)zirconium dihydride; (trifluoromethylcyclopentadienyl)(cyclopentadienyl)hafnium dimethyl; (trifluoromethyl-cyclopentadienyl)(cyclopentadienyl)titanium dimethyl; (trifluoromethylcyclopentadienyl)-(cyclopentadienyl)zirconium dimethyl; (trimethylcyclopentadienyl)(cyclopentadienyl)hafnium dihydride; (trimethylcyclopentadienyl)(cyclopentadienyl)hafnium dimethyl; (trimethylcyclopentadienyl)(cyclopentadienyl)titanium dihydride; (trimethylcyclopentadienyl)(cyclopentadienyl)titanium dimethyl; (trimethylcyclopentadienyl)(cyclopentadienyl)zirconium dihydride; (trimethylcyclo-pentadienyl)-(cyclopentadienyl)zirconium dimethyl; (trimethylgermylcyclopentadienyl)(cyclopentadienyl) hafnium dihydride; (trimethylgermylcyclopentadienyl)(cyclopentadienyl)titanium dihydride; (trimethylgermyl-cyclopentadienyl)(cyclopentadienyl)-zirconium dihydride; (trimethylgermylcyclopentadienyl)(cyclopentadienyl)-hafnium dimethyl; (trimethylgermylcyclopentadienyl)(cyclopentadienyl)titanium dimethyl; (trimethylgermyl-cyclopentadienyl)(cyclopentadienyl)zirconium dimethyl; (trimethylplumbylcyclopentadienyl)(cyclopentadienyl) hafnium dihydride; (trimethylplumbylcyclopentadienyl)(cyclopentadienyl)titanium dihydride; (trimethylplumbyl-cyclopentadienyl)(cyclopentadienyl)zirconium dihydride; (trimethylplumbylcyclopentadienyl)(cyclopentadienyl) hafnium dimethyl; (trimethylplumbylcyclopentadienyl)(cyclopentadienyl)titanium dimethyl; (trimethylplumbyl cyclopentadienyl)(cyclopentadienyl)zirconium dimethyl; (trimethylsilylcyclopentadienyl)(cyclopentadienyl)hafnium dihydride; (trimethylsilylcyclopentadienyl)(cyclopentadienyl)hafnium dimethyl; (trimethylsilyl-cyclopentadienyl)-(cyclopentadienyl)titanium dihydride; (trimethylsilylcyclopentadienyl)(cyclopentadienyl)titanium dimethyl; (trimethylsilylcyclopentadienyl)(cyclopentadienyl)zirconium dihydride; (trimethylsilyl-cyclopentadienyl)(cyclopentadienyl)-zirconium dimethyl; (trimethylstannylcyclopentadienyl)(cyclopentadienyl)-hafnium dihydride; (trimethylstannylcyclopentadienyl)(cyclopentadienyl)titanium dihydride; (trimethylstannyl-cyclopentadienyl)(cyclopentadienyl)zirconium dihydride; [1,1'-(1,1,2,2-tetramethyldisilanylene)bis(3-methylcyclopentadienyl)] zirconium dimethyl; [1,1'-(1,1,2, 2-tetramethyldisilanylene)bis(3-trimethyl-silanylcyclopentadienyl)] zirconium dimethyl; [1,1'-(1,1,2, 2-tetramethyl-disilanylene)-bis(4,5,6,7-tetrahydroindenyl)] hafnium dimethyl; [1,1'-(1,1,2,2-tetramethyldisilanylene)-bis(4,5,6,7-tetrahydroindenyl)] titanium dimethyl; [1,1'-(1, 1,2,2-tetramethyldisilanylene)-bis(4,5,6,7-tetrahydroindenyl)] zirconium dimethyl; [1,1'-(1,1,3,3-tetramethyldisiloxanylene)bis(4,5,6,7-tetrahydroindenyl)] hafnium dimethyl; [1,1'-(1,1,3,3-tetramethyldisiloxanylene) bis(4,5,6,7-tetrahydroindenyl)] titanium dimethyl; [1,1'-(1, 1,3,3-tetramethyldisiloxanylene)-bis(4,5,6,7-tetrahydroindenyl)] zirconium dimethyl; [1,1'-(1,1,4,4-tetramethyl-1,4-disilanylbutylene)bis(4,5,6,7-tetrahydroindenyl)] hafnium dimethyl; [1,1'-1,1,4,4-tetramethyl-1,4-disilanylbutylene)bis(4,5,6,7-tetrahydroindenyl)] titanium dimethyl; [1,1'-(1,1,4,4-tetramethyl-1,4-disilanylbutylene)bis(4,5,6,7-tetrahydroindenyl)] zirconium dimethyl; [1,1'-(2,2-dimethyl-2-silapropylene)-bis-(3-methylcyclopentadienyl)] hafnium dimethyl; [1,1'-(2,2-dimethyl-2-silapropylene)-bis (3-methylcyclopentadienyl)[titanium dimethyl; [1,1'-(2,2-dimethyl-2-silapropylene)-bis(3-methylcyclopentadienyl)] zirconium dimethyl; [1,1'-dimethylsilanylenebis(3-methylcyclopentadienyl)] hafnium dimethyl; [1,1'-dimethylsilanylenebis(3-methylcyclopentadienyl)] titanium dimethyl; [1,1'-dimethylsilanylenebis(3-methylcyclo-pentadienyl)] zirconium dimethyl; [1,1'-dimethylsilanylene-bis(3-trimethylsilanylcyclopentadienyl)] hafnium dimethyl; [1,1'-dimethylsilanylene-bis(3-trimethylsilanylcyclopentadienyl)] titanium dimethyl; [1,1'-dimethylsilanylene-bis(3-trimethylsilanylcyclopentadienyl)] zirconium dimethyl; [1,1'-dimethylsilanylene-bis(4,5,6,7-tetrahydroindenyl)] hafnium dimethyl; [1,1'-dimethylsilanylene-bis(4,5,6,7-tetrahydroindenyl)] titanium dimethyl; [1,1'-dimethylsilanylene-bis(4,5,6,7-tetrahydroindenyl)] zirconium dimethyl; [1,1'-dimethylsilanylene-bis(indenyl)] hafnium dimethyl; [1,1'-dimethylsilanylene-bis(indenyl)] titanium dimethyl; [1,1'- dimethylsilanylene-bis(indenyl)] zirconium dimethyl; bis(benzylcyclopentadienyl)hafnium dihydride; bis-(benzylcyclopentadienyl)hafnium dimethyl; bis(benzylcyclopentadienyl)titanium dihydride; bis(benzylcyclopentadienyl)titanium dimethyl; bis(benzylcyclopentadienyl)zirconium dihydride; bis(benzylcyclopentadienyl)zirconium dimethyl; bis-(cyclohexylmethylcyclopentadienyl)hafnium dihydride; bis(cyclohexylmethylcyclopentadienyl)hafnium dimethyl; bis(cyclohexylmethylcyclopentadienyl)-titanium dihydride; bis(cyclohexylmethylcyclopentadienyl)titanium dimethyl; bis-(cyclohexylmethylcyclopentadienyl)zirconium dihydride; bis(cyclohexylmethylcyclopentadienyl)zirconium dimethyl; bis(cyclopentadienyl)(trimethylsilyl)-(methyl)hafnium; bis(cyclopentadienyl)(trimethylsilyl)(methyl)titanium; bis-(cyclopentadienyl)(trimethylsilyl)(methyl)zirconium; bis(cyclopentadienyl)[tris-(dimethylsilyl)silyl](methyl)hafnium; bis(cyclopentadienyl)[tris(dimethylsilyl)silyl](methyl)titanium; bis(cyclopentadienyl)[tris(dimethylsilyl)silyl](methyl)-zirconium; bis(cyclopentadienyl)(trimethylsilyl)(tris(trimethylsilyl)(trimethylsilylbenzyl); bis(cyclopentadienyl)(triphenylsilyl)(methyl)hafnium; bis(cyclopentadienyl)(triphenylsilyl)(methyl)titanium; bis(cyclopentadienyl)(triphenylsilyl)(methyl)zirconium; bis(cyclopentadienyl)hafnium di(m-tolyl); bis(cyclopentadienyl)hafnium di(p-tolyl); bis(cyclopentadienyl)hafnium dibutyl; bis(cyclopentadienyl)hafnium diethyl; bis(cyclopentadienyl)hafnium dihydride; bis(cyclopentadienyl)hafnium dimethyl; bis(cyclopentadienyl)hafnium dineopentyl; bis(cyclopentadienyl)hafnium diphenyl; bis(cyclopentadienyl)hafnium dipropyl; bis(cyclopentadienyl)titanium di(m-tolyl); bis(cyclopentadienyl)titanium di(p-tolyl); bis-(cyclopentadienyl)titanium dibutyl; bis(cyclopentadienyl)titanium diethyl; bis-(cyclopentadienyl)titanium dihydride; bis(cyclopentadienyl)titanium dimethyl; bis(cyclopentadienyl)titanium dineopentyl; bis(cyclopentadienyl)titanium diphenyl; bis(cyclopentadienyl)titanium dipropyl; bis(cyclopentadienyl)zirconium di(m-tolyl); bis(cyclopentadienyl)zirconium di(p-tolyl); bis(cyclopentadienyl)-zirconium dibutyl; bis(cyclopentadienyl)zirconium diethyl; bis(cyclopentadienyl)-zirconium dihydride; bis(cyclopentadienyl)zirconium dimethyl; bis(cyclopentadienyl)zirconium dineopentyl; bis(cyclopentadienyl)zirconium diphenyl; bis-(cyclopentadienyl)zirconium dipropyl; bis-(dimethylcyclopentadienyl)hafnium dihydride; bis(dimethylcyclopentadienyl)hafnium dimethyl; bis(dimethylcyclopentadienyl)titanium dihydride; bis(dimethylcyclopentadienyl)titanium dimethyl; bis(dimethylcyclopentadienyl)zirconium dihydride; bis(dimethylcyclopentadienyl)zirconium dimethyl; bis(diphenylmethylcyclopentadienyl)hafnium dihydride; bis(diphenylmethylcyclopentadienyl)hafnium dimethyl; bis(diphenylmethylcyclopentadienyl)titanium dihydride; bis(diphenylmethylcyclopentadienyl)titanium dimethyl; bis(diphenylmethylcyclopentadienyl)zirconium dihydride; bis(diphenylmethylcyclopentadienyl)zirconium dimethyl; bis(ethylcyclopentadienyl)hafnium dimethyl; bis(ethylcyclopentadienyl)titanium dimethyl; bis-(ethylcyclopentadienyl)zirconium dimethyl; bis(ethyltetramethylcyclopentadienyl)hafnium dimethyl; bis(ethyltetramethylcyclopentadienyl)titanium dimethyl; bis(ethyltetramethylcyclopentadienyl)zirconium dimethyl; bis(ethyltetramethylcyclopentadienyl)hafnium dihydride; bis(ethyltetramethylcyclopentadienyl)titanium dihydride; bis(ethyltetramethylcyclopentadienyl)zirconium dihydride; bis(indenyl)hafnium dimethyl; bis(indenyl)titanium dihydride; bis(indenyl)titanium dimethyl; bis(indenyl)zirconium dihydride; bis(indenyl)zirconium dimethyl; bis(methylcyclopentadienyl)hafnium dimethyl; bis(methylcyclopentadienyl)titanium dimethyl; bis(methylcyclopentadienyl)zirconium dimethyl; bis(methylcyclopentadienyl)hafnium dihydride; bis-(methylcyclopentadienyl)titanium dihydride; bis(methylcyclopentadienyl)-zirconium dihydride; bis(n-butylcyclopentadienyl)hafnium dimethyl; bis(n-butylcyclopentadienyl)titanium dimethyl; bis(n-butylcyclopentadienyl)zirconium dimethyl; bis(n-butylcyclopentadienyl)hafnium dihydride; bis(n-butylcyclopentadienyl)titanium dihydride; bis(n-butylcyclopentadienyl)zirconium dihydride; bis-(pentamethylcyclopentadienyl)(benzyne)hafnium; bis(pentamethylcyclopentadienyl)(benzyne)titanium; bis(pentamethylcyclopentadienyl)(benzyne)zirconium; bis(pentamethylcyclopentadienyl)hafnium dimethyl; bis(pentamethylcyclopentadienyl)titanium dimethyl; bis(pentamethylcyclopentadienyl)zirconacyclopentane; bis(pentamethylcyclopentadienyl)zirconium dimethyl; bis(pentamethylcyclopentadienyl)hafnium (methyl)(hydride); bis(pentamethylcyclopentadienyl)hafnium (phenyl)(hydride); bis(pentamethylcyclopentadienyl)hafnium dihydride; bis-(pentamethylcyclopentadienyl)titanium (methyl)(hydride); bis(pentamethylcyclopentadienyl)titanium (phenyl)(hydride); bis(pentamethylcyclopentadienyl)-titanium dihydride; bis(pentamethylcyclopentadienyl)zirconacyclobutane; bis-(pentamethylcyclopentadienyl)zirconium (methyl)(hydride); bis(pentamethylcyclopentadienyl)zirconium (phenyl)(hydride); bis(pentamethylcyclopentadienyl)-zirconium dihydride; bis(propylcyclopentadienyl)hafnium dimethyl; bis-(propylcyclopentadienyl)titanium dimethyl; bis(propylcyclopentadienyl)zirconium dimethyl; bis(propylcyclopentadienyl)hafnium dihydride; bis(propylcyclopentadienyl)titanium dihydride; bis(propylcyclopentadienyl)zirconium dihydride; bis(t-butylcyclopentadienyl)hafnium dimethyl; bis(t-butylcyclopentadienyl)titanium dimethyl; bis(t-butylcyclopentadienyl)zirconium dimethyl; bis(t-butylcyclopentadienyl)hafnium dihydride; bis(t-butylcyclopentadienyl)titanium dihydride; bis(t-butylcyclopentadienyl)zirconium dihydride; bis(tetramethylcyclopentadienyl)-hafnium dihydride; bis(tetramethylcyclopentadienyl)hafnium dimethyl; bis-(tetramethylcyclopentadienyl)titanium dihydride; bis(tetramethylcyclopentadienyl)titanium dimethyl; bis(tetramethylcyclopentadienyl)zirconium dihydride; bis(tetramethylcyclopentadienyl)zirconium dimethyl; bis(trifluoromethylcyclopentadienyl)hafnium dihydride; bis(trifluoromethylcyclopentadienyl)hafnium dimethyl; bis(trifluoromethylcyclopentadienyl)titanium dihydride; bis-(trifluoromethylcyclopentadienyl)titanium dimethyl; bis(trifluoromethylcyclopentadienyl)zirconium dihydride; bis(trifluoromethylcyclopentadienyl)zirconium dimethyl; bis(trimethylcyclopentadienyl)hafnium dihydride; bis(trimethylcyclopentadienyl)hafnium dimethyl; bis(trimethylcyclopentadienyl)titanium dihydride; bis(trimethylcyclopentadienyl)titanium dimethyl; bis(trimethylcyclopentadienyl)-zirconium dihydride; bis(trimethylcyclopentadienyl)zirconium dimethyl; bis-(trimethylgermylcyclopentadienyl)hafnium dihydride; bis(trimethylgermylcyclopentadienyl)hafnium dimethyl; bis(trimethylgermylcyclopentadienyl)titanium dihydride; bis(trimethylgermylcyclopentadienyl)titanium dimethyl; bis (trimethylgermylcyclopentadienyl)zirconium dihydride; bis (trimethylgermylcyclopentadienyl)zirconium dimethyl; bis(trimethylplumbylcyclopentadienyl)hafnium dihydride; bis(trimethylplumbylcyclopentadienyl)hafnium dimethyl; bis(trimethylplumbylcyclopentadienyl)titanium dihydride; bis(trimethylplumbylcyclopentadienyl)titanium dimethyl; bis(trimethylplumbylcyclopentadienyl)zirconium dihydride; bis(trimethylplumbylcyclopentadienyl)zirconium dimethyl; bis(trimethylsilylcyclopentadienyl)hafnium dihydride; bis(trimethylsilylcyclopentadienyl)-hafnium dimethyl; bis(trimethylsilylcyclopentadienyl)titanium dihydride; bis-(trimethylsilylcyclopentadienyl)titanium dimethyl; bis(trimethylsilylcyclopentadienyl)zirconium dihydride; bis(trimethylsilylcyclopentadienyl)zirconium dimethyl; bis(trimethylstannylcyclopentadienyl)hafnium dihydride; bis(trimethylstannylcyclopentadienyl)titanium dihydride; bis(trimethylstannylcyclopentadienyl)zirconium dihydride; dibutylsilyl (fluorenyl)(cyclopentadienyl)hafnium dimethyl; diethylsilanediylbis-2-methylindenyl)-zirconium diethyl; diethylsilane-diylbis-2-methylindenyl)-zirconium dimethyl; dimethylsilanediylbis-2-ethyl-5-isopropylcyclopentadienyl)-zirconium dimethyl; dimethylsilanediylbis-(2-ethyl-indenyl)-zirconium dimethyl; dimethylsilanediylbis-(2-isopropylindenyl)-zirconium dimethyl; dimethylsilanediylbis-(2-methyl-5-ethylcyclopentadienyl)-zirconium dimethyl; dimethylsilanediylbis-(2-methyl-5-methylcyclopentadienyl)-zirconium dimethyl; dimethylsilanediylbis-2-methylbenzindenyl)-zirconium dimethyl; dimethylsilanediylbis-(2-methylindanyl)-zirconium dimethyl; dimethylsilanediylbis-(2-methylindenyl)-hafnium dimethyl; dimethylsilanediylbis-2-methylindenyl)-zirconium dimethyl; dimethylsilanediylbis-(2-t-butylindenyl)-zirconium dimethyl; dimethylsilyl (indenyl)(fluorenyl)hafnium dihydride; dimethylsilyl bis(2-methyl-indenyl)hafnium dimethyl; dimethylsilyl bis(2-propyl-indenyl)hafnium dimethyl; dimethylsilyl bis(4-methyl, 2-phenyl-indenyl)hafnium dimethyl; dimethylsilyl bis(cyclopentadienyl)hafnium dihydride; dimethylsilyl bis(cyclopentadienyl)titanium dihydride; dimethylsilyl bis(cyclopentadienyl)zirconium dihydride; dimethylsilyl bis(indenyl)hafnium dimethyl; dimethylsilyl (methylcyclopentadienyl)(1-fluorenyl)hafnium dihydride; dimethylsilyl(methylcyclopentadienyl)(1-fluorenyl)titanium dihydride; dimethylsilyl(methylcyclopentadienyl)(1-fluorenyl)zirconium dihydride; dimethylsilylbis-(3-trimethylsilylcyclopentadienyl)hafnium dihydride; dimethylsilylbis(3-trimethylsilylcyclopentadienyl)titanium dihydride; dimethylsilylbis(3-trimethylsilylcyclopentadienyl)zirconium dihydride; dimethylsilylbis(indenyl)hafnium dimethyl; dimethylsilylbis(indenyl)titanium dimethyl; dimethylsilylbis(indenyl)-zirconium dimethyl; dimethylthiobis-(2-methylindenyl)-zirconium dimethyl; dinapthylmethylene (cyclopentadienyl)(fluorenyl)hafnium dimethyl; diphenylmethylene (2,7-di-n-butyl fluorenyl)(cyclopentadienyl)hafnium dimethyl; diphenylmethylene (2,7-di-n-butyl fluorenyl)(fluorenyl)hafnium dimethyl; diphenylmethylene (2,7-di-t-butyl fluorenyl)(cyclopentadienyl)hafnium dimethyl; diphenylmethylene (2,7-di-t-butyl fluorenyl)(fluorenyl)hafnium dimethyl; diphenylmethylene (2,7-di-t-butyl-5-methylfluorenyl)(cyclopentadienyl)hafnium dimethyl; diphenylmethylene (cyclopentadienyl)(2,7-dimethylfluorenyl)hafnium dimethyl; diphenylmethylene (cyclopentadienyl)(2,7-di-t-butyl fluorenyl)hafnium dimethyl; diphenylmethylene (indenyl)(2,7-di-t-butyl fluorenyl)hafnium dibenzyl; ethylene bis(cyclopentadienyl)hafnium dihydride; ethylene bis(cyclopentadienyl)-hafnium dihydride; dimethylsilyl bis(cyclopentadienyl)hafnium dihydride; ethylene bis(cyclopentadienyl)hafnium dimethyl; ethylene bis(cyclopentadienyl)-titanium dihydride; ethylene bis(cyclopentadienyl)titanium dihydride; dimethylsilyl bis(cyclopentadienyl)titanium dihydride; ethylene bis(cyclopentadienyl)-titanium dimethyl; ethylene bis(cyclopentadienyl)zirconium dihydride; ethylene bis(cyclopentadienyl)zirconium dihydride; ethylene bis(cyclopentadienyl)-zirconium dimethyl; ethylenebis(indenyl)hafnium dimethyl; ethylenebis(indenyl)-titanium dimethyl; ethylenebis(indenyl)zirconium dimethyl; ethylenebis-(tetrahydroindenyl)hafnium dimethyl; ethylenebis(tetrahydroindenyl)titanium dimethyl; ethylenebis(tetrahydroindenyl)zirconium dimethyl; i-propyl (cyclopentadienyl)(fluorenyl)hafnium dimethyl; isopropyl (cyclopentadienyl)(1-fluorenyl)-hafnium dimethyl; isopropyl(cyclopentadienyl)(1-fluorenyl)titanium dimethyl; isopropyl(cyclopentadienyl)(1-fluorenyl)zirconium dimethyl; isopropyl(cyclopentadienyl)(1-octahydro-fluorenyl) hafnium dimethyl; isopropyl(cyclopentadienyl)(1-octahydro-fluorenyl)titanium dimethyl; isopropyl (cyclopentadienyl)(1-octahydro-fluorenyl)zirconium dimethyl; methylene (2,7-di-t-butyl fluorenyl)-(fluorenyl) hafnium dimethyl; methylene (indenyl)(2,7-di-t-butyl-fluorenyl)-hafnium dimethyl; methylene bis(cyclopentadienyl)hafnium dimethyl; methylene bis(cyclopentadienyl)titanium dimethyl; methylene bis(cyclopentadienyl)-zirconium dimethyl; methylene bis(fluorenyl)hafnium dimethyl; methylene(cyclopentadienyl (tetramethylcyclopentadienyl)hafnium dimethyl; methylene(cyclopentadienyl (tetramethylcyclopentadienyl)titanium dimethyl; methylene(cyclopentadienyl (tetramethylcyclopentadienyl)zirconium dimethyl; methylene (cyclopentadienyl)(1-fluorenyl)hafnium dihydride; methylene(cyclopentadienyl)(1-fluorenyl)titanium dihydride; methylene(cyclopentadienyl)(1-fluorenyl)zirconium dihydride; methylphenylmethylene bis(fluorenyl)hafnium dimethyl; bis(methylcyclopentadienyl)zirconium dimethyl; bis(ethylcyclopentadienyl)zirconium dimethyl; bis(methylcyclopentadienyl)zirconium dimethyl; bis(ethylcyclopentadienyl)zirconium dimethyl; bis(methylcyclopentadienyl)zirconium dihydride; bis-(ethylcyclopentadienyl)zirconium dihydride; bis(dimethylcyclopentadienyl)-zirconium dimethyl; bis(trimethylcyclopentadienyl)zirconium dimethyl; bis-(tetramethylcyclopentadienyl)zirconium dimethyl; bis(ethyltetramethylcyclopentadienyl)zirconium dimethyl; bis(indenyl)zirconium dimethyl; bis(dimethylcyclopentadienyl)zirconium dimethyl; bis(trimethylcyclopentadienyl)zirconium dimethyl; bis(tetramethylcyclopentadienyl)zirconium dimethyl; bis(ethyltetramethylcyclopentadienyl)zirconium dimethyl; bis(indenyl)zirconium dimethyl; bis(dimethylcyclopentadienyl)zirconium dihydride; bis(trimethylcyclopentadienyl)zirconium dihydride; bis(ethyltetramethylcyclopentadienyl)zirconium dihydride; bis(trimethylsilylcyclopentadienyl)zirconium dimethyl; bis(trimethylsilylcyclopentadienyl)zirconium dihydride; bis(trifluoromethylcyclopentadienyl) zirconium dimethyl; bis(trifluoromethylcyclopentadienyl)zirconium dimethyl; bis-(trifluoromethylcyclopentadienyl)zirconium dihydride; isopropylidene-bis-(indenyl)zirconium dimethyl; isopropylidene-bis(indenyl)zirconium dimethyl; isopropylidene-bis(indenyl)zirconium dihydride; pentamethylcyclopentadienyl(cyclopentadienyl)zirconium dimethyl; pentamethylcyclopentadienyl(cyclopentadienyl) zirconium dimethyl; pentamethylcyclopentadienyl (cyclopentadienyl)-zirconium dihydride;

ethyltetramethylcyclopentadienyl(cyclopentadienyl)-zirconium dihydride; isopropylidene(cyclopentadienyl)(fluorenyl)zirconium dimethyl; isopropylidene(cyclopentadienyl)(fluorenyl)zirconium dimethyl; dimethylsilyl(cyclopentadienyl)(fluorenyl)zirconium dimethyl; isopropylidene(cyclopentadienyl)(fluorenyl)zirconium dihydride, bis(cyclopentadienyl)zirconium dimethyl; bis(cyclopentadienyl)zirconium dimethyl; bis(cyclopentadienyl)zirconium diethyl; bis(cyclopentadienyl)zirconium dipropyl; bis(cyclopentadienyl)zirconium diphenyl; methylcyclopentadienyl(cyclopentadienyl)zirconium dimethyl; ethylcyclopentadienyl(cyclopentadienyl)zirconium dimethyl; methylcyclopentadienyl(cyclopentadienyl)zirconium dimethyl; ethylcyclopentadienyl(cyclopentadienyl)zirconium dimethyl; methylcyclopentadienyl(cyclopentadienyl)zirconium dihydride; ethylcyclopentadienyl(cyclopentadienyl)zirconium dihydride; dimethylcyclopentadienyl(cyclopentadienyl)zirconium dimethyl; trimethylcyclopentadienyl(cyclopentadienyl)zirconium dimethyl; tetramethylcyclopentadienyl(cyclopentadienyl)zirconium dimethyl; bis(pentamethylcyclopentadienyl)zirconium dimethyl; tetramethylcyclopentadienyl(cyclopentadienyl)zirconium dimethyl; indenyl(cyclopentadienyl)zirconium dimethyl; dimethylcyclopentadienyl(cyclopentadienyl)zirconium dimethyl; trimethylcyclopentadienyl(cyclopentadienyl)-zirconium dimethyl; tetramethylcyclopentadienyl(cyclopentadienyl)zirconium dimethyl; bis(pentamethylcyclopentadienyl)zirconium dimethyl; ethyltetramethylcyclopentadienyl(cyclopentadienyl)zirconium dimethyl; indenyl(cyclopentadienyl)zirconium dimethyl; dimethylcyclopentadienyl(cyclopentadienyl)-zirconium dihydride; trimethylcyclopentadienyl(cyclopentadienyl)zirconium dihydride; bis(pentamethylcyclopentadienyl)zirconium dihydride; indenyl(cyclopentadienyl)zirconium dihydride; trimethylsilylcyclopentadienyl(cyclopentadienyl)zirconium dimethyl; trimethylsilylcyclopentadienyl(cyclopentadienyl)-zirconium dihydride; trifluoromethylcyclopentadienyl(cyclopentadienyl)-zirconium dimethyl; trifluoromethylcyclopentadienyl(cyclopentadienyl)zirconium dimethyl; trifluoromethylcyclopentadienyl(cyclopentadienyl)zirconium dihydride; bis(cyclopentadienyl)(trimethylsilyl)(methyl)zirconium; bis(cyclopentadienyl)-(triphenylsilyl)(methyl)zirconium; bis(cyclopentadienyl)[tris(dimethylsilyl)-silyl](methyl)zirconium; bis(cyclopentadienyl)[bis(methylsilyl)silyl](methyl)-zirconium; bis(cyclopentadienyl)(trimethylsilyl)(trimethylsilyl methyl)zirconium; bis(cyclopentadienyl)(trimethylsilyl)(benzyl)zirconium; methylene-bis(cyclopentadienyl)zirconium dimethyl; ethylene-bis(cyclopentadienyl)zirconium dimethyl; isopropylidene-bis(cyclopentadienyl)zirconium dimethyl; dimethylsilyl-bis(cyclopentadienyl)zirconium dimethyl; methylene-bis(cyclopentadienyl)-zirconium dimethyl; ethylene-bis(cyclopentadienyl)zirconium dimethyl; isopropylidene-bis(cyclopentadienyl)zirconium dimethyl; dimethylsilyl-bis(cyclopentadienyl)zirconium dimethyl; methylene-bis(cyclopentadienyl)zirconium dihydride; ethylene-bis(cyclopentadienyl)zirconium dihydride; isopropylidene-bis(cyclopentadienyl)zirconium dihydride; dimethylsilyl-bis(cyclopentadienyl)zirconium dihydride; (Pentamethylcyclopentadienyl)zirconium trimethyl; (Pentamethylcyclopentadienyl)zirconium triphenyl; (Pentamethylcyclopentadienyl)zirconium tribenzyl; (Pentamethylcyclopentadienyl)zirconium trimethyl; (Cyclopentadienyl)zirconium trimethyl; (Cyclopentadienyl)zirconium triphenyl; (Cyclopentadienyl)zirconium tribenzyl; (Cyclopentadienyl)zirconium trimethyl; (Methylcyclopentadienyl)zirconium trimethyl; (Methylcyclopentadienyl)zirconium triphenyl; (Methylcyclopentadienyl)zirconium tribenzyl; (Methylcyclopentadienyl)-zirconium trimethyl; (Dimethylcyclopentadienyl)zirconium trimethyl; (Trimethylcyclopentadienyl)zirconium trimethyl; (Trimethylsilylcyclopentadienyl)zirconium trimethyl; (Tetramethylcyclopentadienyl)zirconium trimethyl; Indenylzirconium trimethyl; Fluorenylzirconium trimethyl; Bis(cyclopentadienyl)zirconium dimethyl; Bis(cyclopentadienyl)zirconium diphenyl; Bis(cyclopentadienyl)-zirconium dibenzyl; Bis(cyclopentadienyl)zirconium dimethyl; Bis(cyclopentadienyl)zirconium diethyl; Bis(cyclopentadienyl)zirconium dihydride; Bis(cyclopentadienyl)zirconium dichlorohydride; Bis(methylcyclopentadienyl)zirconium dimethyl; Bis(methylcyclopentadienyl)zirconium diphenyl; Bis-(methylcyclopentadienyl)zirconium dibenzyl; Bis(methylcyclopentadienyl)-zirconium dimethyl; Bis(pentamethylcyclopentadienyl)zirconium dimethyl; Bis-(pentamethylcyclopentadienyl)zirconium dimethyl; Bis(pentamethylcyclopentadienyl)zirconium dibenzyl; Bis(pentamethylcyclopentadienyl)zirconium methyl-methyl; Bis(pentamethylcyclopentadienyl)zirconium methylhydride; Ethylenebis-(indenyl)zirconium dimethyl; Ethylenebis(indenyl)zirconium dimethyl; Ethylenebis(tetrahydroindenyl)zirconium dimethyl; Ethylenebis(tetrahydroindenyl)-zirconium dimethyl; Dimethylsilylenebis(cyclopentadienyl)zirconium dimethyl; Dimethylsilylenebis(cyclopentadienyl)zirconium dimethyl; Isopropylidene(cyclopentadienyl)(9-fluorenyl)zirconium dimethyl; Phenylmethylmethylene(cyclopentadienyl)(9-fluorenyl)zirconium dimethyl; Diphenylmethylene(cyclopentadienyl)(9-fluorenyl)zirconium dimethyl; Ethylene(cyclopentadienyl)(9-fluorenyl)-zirconium dimethyl; Cyclohyxylidene(cyclopentadienyl)(9-fluorenyl)zirconium dimethyl; Cyclopentylidene(cyclopentadienyl)(9-fluorenyl)zirconium dimethyl; Cyclobutylidene(cyclopentadienyl)(9-fluorenyl)zirconium dimethyl; Dimethylsilylene(cyclopentadienyl)(9-fluorenyl)zirconium dimethyl; Dimethylsilylenebis-(2,3,5-trimethylcyclopentadienyl)zirconium dimethyl; Dimethylsilylenebis(2,3,5-trimethylcyclopentadienyl)zirconium dimethyl; Dimethylsilylenebis(indenyl)-zirconium dimethyl; Zirconium tetramethyl; Zirconium tetrabenzyl; Zirconium tetramethyl; Zirconium tetramethyl; Zirconium butoxytrimethyl; Zirconium dibutoxydimethyl; Bis(2,5-di-t-butylphenoxy)zirconium dimethyl; Bis(2,5-di-t-butylphenoxy)zirconium dimethyl; Zirconium bis(acetylacetonate)dimethyl; dimethylsilyl(tetramethylclopentadienyl)cycldodecyloamido)titanium dimethyl; dimethylsilyl(tetra-methyleyclopentadienyl)(1-adamantylamido)titanium dimethyl; dimethylsilyl(tetramethylcyclopentadienyl)(t-butylamido)titanium dimethyl; cyclopentadienylzirconium trimethyl; cyclopentadienylzirconium triethyl; cyclopentadienylzirconium tripropyl; cyclopentadienyltitanium trimethyl; cyclopentadienyltitanium triphenyl; cyclopentadienylscandium bis(p-tolyl); cyclopentadienylchromium 2,4-pentadienyl; (pentamethylcyclopentadienyl)yttrium bis(bis-trimethylsilylmethyl); (pentamethylcyclopentadienyl)scandium bis(bistrimethylsilylmethyl); pentamethylcyclopentadienyl lanthanum bis(bistrimethylsilylmethyl); [1,1'- dimethylsilanylene-bis(2-methyl-indenyl)) hafnium dimethyl; [1,1'-dimethylsilanylene-bis(2-methy-4-phenyl-lindenyl)] hafnium dimethyl; [1,1'-dimethylsilanylene-bis (2-methy-4-naphth-2-yl-lindenyl)] hafnium dimethyl; diphenylmethylene (cyclopentadienyl)(fluorenyl)hafnium dimethyl; [(4-n-butylphenyl)(4-t-butylphenyl)methylene] (cyclopentadienyl)(fluorenyl)hafnium dimethyl; dimethylsilanylene (tetramethylcyclopentadienyl)(N-adamantylamido)-titanium dimethyl; dimethylsilanylene (tetramethylcyclopentadienyl)(N-t-butylamido)titanium dimethyl; bis(4-[triethylsilyl])methylene (cyclopentadienyl)-(fluorenyl)hafnium dimethyl; bis(4-[triethylsilyl])methylene (cyclopentadienyl)-(2,7-di-t-butylfluorenyl)hafnium dimethyl.

Additional compounds suitable as olefin polymerization catalysts for use in this invention will be any of those Group-3–10 compounds that can be converted by ligand abstraction or bond scission into a cationic catalyst and stabilized in that state by a noncoordinating or weakly coordinating anion sufficiently labile to be displaced by an olefinically unsaturated molecules such as ethylene.

Exemplary compounds include those described in the patent literature. International patent publications WO 96/23010, WO 97/48735 and Gibson, et al., *Chem. Comm.*, pp. 849–850 (1998), which disclose diimine-based ligands for Group-8 to -10 compounds that undergo ionic activation and polymerize olefins. Polymerization catalyst systems from Group-5–10 metals, in which the active center is highly oxidized and stabilized by low-coordination-number, polyanionic, ligand systems, are described in U.S. Pat. No. 5,502,124 and its divisional U.S. Pat. No. 5,504,049. See also the Group-5 organometallic catalyst compounds of U.S. Pat. No. 5,851,945 and the tridentate-ligand-containing, Group-5–10, organometallic catalysts of copending U.S. application Ser. No. 09/302,243, filed 29 Apr. 1999, and its equivalent PCT/US99/09306. Group-11 catalyst precursor compounds, activable with ionizing cocatalysts, useful for olefin and vinylic polar molecules are described and exemplified in WO 99/30822 and its priority documents, including U.S. patent application Ser. No. 08/991,160, filed 16 Dec.
1997.

U.S. Pat. No. 5,318,935 describes bridged and unbridged, bisamido catalyst compounds of Group-4 metals capable of α-olefins polymerization. Bridged bis(arylamido) Group-4 compounds for olefin polymerization are described by D. H. McConville, et al., in *Organometallics* 1995, 14, 5478–5480. Synthetic methods and compound characterization are presented. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition metal compounds include those described in WO 96/40805. Cationic Group-3- or Lanthanide-metal olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors, which can be activated with this invention's ionic cocatalysts.

The literature contains many additional descriptions of suitable catalyst-precursor compounds. Compounds that contain abstractable ligands or that can be alkylated to contain abstractable ligands are suitable for the practice of this invention. See, for instance, V. C. Gibson, et al; "The Search for New-Generation Olefin Polymerization Catalysts: Life Beyond Metallocenes", *Angew. Chem. Int. Ed.*, 38, 428–447 (1999).

When using the above catalysts, the catalyst system will generally employ one or more scavenging agents to remove polar impurities from the reaction environment and to increase catalyst activity. Any polymerization reaction components, particularly solvents, monomers, and catalyst feedstreams, can inadvertently introduce impurities and adversely affect catalyst activity and stability. Impurities decrease or even eliminate catalytic activity, particularly with ionizing-anion-activated catalyst systems. Polar impurities, or catalyst poisons, include water, oxygen, metal impurities, etc. These impurities can be removed from or reduced in the reaction components before their addition to the reaction vessel. Impurities can be removed by chemically treating the components or by impurity separation steps. Such treatment or separation can occur during or after synthesis of the components. In any case, the polymerization process will normally employ minor amounts of scavenging agent. Typically, these scavengers will be organometallic such as the Group-13 compounds of U.S. Pat. Nos. 5,153, 157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, and isobutyl alumoxane. Those compounds having bulky or $C_{6-C20}$ linear hydrocarbyl substituents connected to the metal or metalloid center are preferred because they coordinate to the active catalyst more weakly. Examples include triethylaluminum and bulky compounds such as tri-isobutyl aluminum, tri-isoprenyl aluminum, and long-chain, linear-alkyl-substituted aluminum compounds, such as tri-n-hexylaluminum, tri-n-octylaluminum, or tri-n-dodecylaluminum. When alumoxane is used as activator, any excess over that needed to activate the catalyst can act as a scavenger and additional organometallic scavengers may be unnecessary. Alumoxanes also may be used as scavengers with other activators, e.g., methylalumoxane and triisobutyl-alumoxane with boron-based activators. The scavenger amount is limited to that amount effective to enhance activity (and with that amount necessary for activation when used in a dual role) since excess amounts may act as catalyst poisons.

This invention's catalyst systems can polymerize those unsaturated molecules conventionally recognized as polymerizable using metallocenes. Typical conditions include solution, slurry, gas-phase, and high-pressure polymerization. The catalysts may be supported on inorganic oxide or polymeric supports and as such will be particularly useful in those operating modes employing fixed-bed, moving-bed, fluid-bed, slurry, or solution processes conducted in single, series, or parallel reactors. Invention cocatalysts may also function in catalyst pre-polymerization. WO 98/55518, describes a support method for gas-phase or slurry polymerization.

Alternative invention embodiments employ the catalyst system in liquid phase (solution, slurry, suspension, bulk phase, or combinations thereof), in high-pressure liquid or supercritical fluid phase, or in gas phase. These processes may also be employed in singular, parallel, or series reactors. The liquid phase processes comprise contacting olefin molecules with the catalyst system described above in a suitable diluent or solvent and allowing those molecules to react long enough to produce the invention polymers. The term polymer encompasses both homo- and co-polymers. Both aliphatic and aromatic hydrocarbyl solvents are suitable; some embodiments select hexane. In bulk and slurry processes, the supported catalysts typically contact a liquid monomer slurry. Gas-phase processes use a supported catalyst and follow any manner suitable for ethylene polymerization, although, some embodiments select the maximum pressure to be as low as 1600 or 500. Illustrative examples may be found in U.S. Pat. Nos. 4,543,399, 4,588,790, 5,028,670, 5,382,638, 5352,749, 5,408,017, 5,436,304, 5,453,471, and 5,463,999, 5,767,208 and WO 95/07942.

The minimum, polymerization reaction temperature is 40° C. Some embodiments select the minimum reaction temperature to be 60° C. The temperature can go as high as 250° C., but some embodiments choose not to exceed 220° C. The minimum reaction pressure is 0.001 bar; although, some embodiments choose the minimum pressure to be as high as 0.1 or 1.0 bar. The maximum pressure is less than or equal to 2500 bar.

Invention catalyst systems can produce various polyethylenes including high- and ultra-high-molecular weight polyethylenes. These polyethylenes can be either homopolymers or copolymers with other α-olefins or α-olefinic or non-conjugated diolefins, e.g. $C_{3-20}$ olefins, diolefins, or cyclic olefins. In some embodiments, a low pressure (typically <50 bar) vessel is used. Invention activated catalysts are slurried with a solvent (typically hexane or toluene). The polyethylenes are produced by adding ethylene, and optionally one or more other monomers, along with the slurried catalyst to the low pressure vessel. The temperature is usually within the 40–250° C. range. Cooling removes polymerization heat. Gas-phase polymerization can be conducted, for example, in a continuous fluid-bed, gas-phase reactor operated at a minimum of 2000 kPa and up to 3000 kPa. The minimum temperature is 60° C.; the maximum temperature is 160° C. The gas-phase reaction uses hydrogen as a reaction modifier at a concentration of no less than 100 PPM. The hydrogen gas concentration should not exceed 200 PPM. The reaction employs a $C_4$–$C_8$ comonomer feedstream and a $C_2$ feedstream. The $C_4$–$C_8$ feedstream goes down to 0.5 mol %. It also may go up to 1.2 mol %. Finally, the $C_2$ feedstream has a minimum concentration of 25 mol %. Its maximum concentration is 35 mol %. See, U.S. Pat. Nos. 4,543,399, 4,588,790, 5,028,670 and 5,405,922 and 5,462,999.

High-molecular-weight, low-crystallinity, ethylene-α-olefin elastomers (including ethylene-cyclic-olefin and ethylene-α-olefin-diolefin elastomers) can be prepared using invention catalyst systems under traditional solution processes or by introducing ethylene into invention catalyst slurries with α-olefin, cyclic olefin, or either or both mixed with other polymerizable and non-polymerizable diluents. Typical ethylene pressures range from 10 to 1000 psig (69–6895 kPa) and the diluent temperature typically remains between 40 and 160° C. The process can occur in one or more stirred tank reactors, operated individually, in series, or in parallel. The general disclosure of U.S. Pat. No. 5,001,205 illustrates general process conditions. See also, international application WO 96/33227 and WO 97/22639.

Besides those specifically described above, other molecules may be polymerized using invention catalyst systems, for example, styrene, alkyl-substituted styrenes, isobutylene and other geminally disubstituted olefins, ethylidene norbornene, norbornadiene, dicyclopentadiene, and other olefinically-unsaturated molecules, including other cyclic olefins, such as cyclopentene, norbornene, alkyl-substituted norbornenes, and vinylic polar, polymerizable molecules. See, for example, U.S. Pat. Nos. 5,635,573, 5,763,556, and WO 99/30822. Additionally, α-olefin macromers of up to 1000 mer units or more may be copolymerized yielding branched olefin polymers. Additionally, activated cation catalysts for oligomerization, dimerization, hydrogenation, olefin/carbon-monoxide copolymerization, hydroformulation, hydrosilation, hydroamination, and related reactions can be activated with invention cocatalysts.

The invention cocatalysts can activate individual catalysts or can activate catalysts mixtures for polymer blends. Adept monomer and catalyst selection yields polymer blends analogous to those using individual catalyst compositions. Polymers having increased MWD (for improved processing) and other benefits available from mixed-catalyst-system polymers can be achieved using invention cocatalysts.

Blended polymer formation can be achieved ex situ through mechanical blending or in situ through using mixed catalyst systems. It is generally believed that in situ blending provides a more homogeneous product and allows the blend to be produced in one step. In-situ blending with mixed catalyst systems involves combining more than one catalyst in the same reactor to simultaneously produce multiple, distinct polymer products. This method requires additional catalyst synthesis, and the various catalyst components must be matched for their activities, the polymer products they generate at specific conditions, and their response to changes in polymerization conditions. Invention cocatalysts can activate mixed catalyst systems.

EXAMPLES

The following examples are presented to illustrate the foregoing discussion. All parts, proportions, and percentages are by weight unless otherwise indicated. Where necessary, the examples were carried out in dry, oxygen-free environments and solvents. Although the examples may be directed to certain embodiments of the present invention, they do not limit the invention in any specific respect. Certain abbreviations are used to facilitate the description. These include standard chemical abbreviations for the elements and certain commonly accepted abbreviations, such as: Me=methyl, Et=ethyl, n-Pr=normal-propyl, t-Bu=tertiary-butyl, Ph=phenyl, pfp =pentafluorophenyl, Cp=cyclopentadienyl, Ind=indenyl, Flu=fluorenyl, TMS=trimethylsilyl, TES= triethylsilyl and THF (or thf)=tetrahydrofuran.

All molecular weights are weight average molecular weight unless otherwise noted. Molecular weights (weight average molecular weight (Mw)) and number average molecular weight (Mn) were measured by Gel Permeation Chromatography (GPC) using a Waters 150 Gel Permeation Chromatograph equipped with a differential refractive index (DRI) and low angle light scattering (LS) detectors. The GPC instrument was calibrated using polystyrene standards. Samples were run in 1,2,4-trichlorobenzene (135° C.) using three Polymer Laboratories PC Gel mixed B columns in series. This general technique is discussed in "Liquid Chromatography of Polymers and Related Materials III" J. Cazes Ed., Marcel Decker, 1981, page 207, which is incorporated by reference for purposes of U.S. patent practice. No corrections for column spreading were employed; but data on generally accepted standards, e.g. National Bureau of Standards Polyethylene 1475, demonstrated a precision with 0.2 units for Mw/Mn as calculated from elution times.

EXAMPLES

Example 1

Synthesis of $HC_6F_4$—CC-Si(i-Pr)$_3$

Sonogashira methodology was employed for the coupling reaction. To 150 milliliters of triethylamine was added Pd(OAc)$_2$ (0.733 grams), P(C$_6$H$_5$)$_3$ (2.55 grams), and CuI (0.880 grams). HC$_5$F$_4$Br (17.00 grams) was added to the mixture, followed by HCCTMS (15.00 grams). After 15 minutes of completing the additions, the mixture turned dark and precipitate was observed. After stirring at room temperature for 20 minutes, the reaction was refluxed for 20 hours. The solids were filtered off. The filtrate were taken up with 300 milliliters of diethylether and washed with 5% HCl (aq). The organic layer were separated and dried with MgSO$_4$. After the required amount of time the drying agent was removed and the solvent volume reduced. Column chromatography removes most of the dark colored impurities. Distillation affords the final product (oil bath at 125 deg C., bp=98 deg C. at 10$^4$ millitorr) as a colorless product (9.80 grams). $^1$H NMR (CDCl$_3$, 25 deg C.): 7.03 (m, 1H), 1.11 (bs, 21H).

Example 2

Synthesis of [Li(Et$_2$O)$_{2.5}$][B(C$_6$F$_4$—CC-Si(i-Pr)$_3$)$_4$]

To a cold solution of HC$_6$F$_4$—CC-Si(i-Pr)$_3$ in diethylether was added BuLi (10 milliliters, 1.6 M, Aldrich). After 5 minutes the solution turned a pale green. The reaction was allowed to stir at −78 deg C. for 1 hour. BCl$_3$ (4.0 milliliter, 1.0 M, Aldrich) was added. The reaction was stirred for 4 hours. The solvent was replaced with methylene chloride and the LiCl removed by filtration. The solvent was reduced and pentane was added to incipient cloudiness. The mixture was chilled overnight and the resulting white crystalline product collected by filtration (2.305 grams). $^1$H NMR (Tol-$d_8$, 25 deg C.): 3.10 (q, 12H), 1.14 (m, 84)

Example 3

Synthesis of [DMAH][B(C$_6$F$_4$—CC-Si(i-Pr)$_3$)$_4$]

To a methylene chloride solution of [Li(Et$_2$O)$_{2.5}$][B(C$_6$F$_4$—CC-Si(i-Pr)$_3$)$_4$] (2.281 grams) was added a solution of DMAHCl (0.236 grams). The resulting LiCl was removed by filtration after stirring for 1 hour. The solvent volume was reduced and the product precipitated out with pentane. The resulting product is a white solid (1.851 grams). $^1$H NMR (CD$_2$Cl$_2$, 25 deg C.): 7.63 (m, 3H), 7.29 (m, 2H), 3.35 (s, 6H), 1.10 (bs, 84H). $^{19}$F NMR (CD$_2$Cl$_2$, 25 deg C.): −133.1, −141.4.

Example 4

Polymerization Reactions

The polymerization reaction of propylene were carried out in a ½ liter, autoclave batch reactor operating at 60° C. The catalyst used was bis(indenyl)dimethylsilyl hafnium dimethyl. In all cases the polymerization solvent was hexanes, while the activation solvent was toluene. Standard runs using [B(C$_6$F$_5$)$_4$][C$_6$H$_5$NMe$_2$H] as the activating cocatalyst were carried out. Trioctylaluminium was used as the scavenger in all runs (25% wt). The scavenger-catalyst mole ratios for these two reactions were less than 10. The polymers were precipitated with isopropyl alcohol and dried in a vacuum oven at 75° C. To constant weights. The polymer melting points were determine with DSC, while the molecular weights were measured by GPC.

Results of Propylene Polymerization Reactions

| Catalyst System | Mw (GPC) | Mn (GPC) | Polymer Yield (g) | Melting Point (° C.) |
|---|---|---|---|---|
| A/B | 305,862 | 176,510 | 5.6 | 139 |
| A/B | 250,514 | 133,629 | 13.3 | 139 |
| A/B | 323,947 | 121,767 | 23.5 | 139 |
| A/B | 754,694 | 171,150 | 6.4 | 141 |
| A/B | 722,561 | 153,870 | 11.7 | 140 |
| A/C | 224,404 | 118,690 | NA | 137 |
| A/C | 306,886 | 126,972 | 27.0 | 137 |

A = Me$_2$Si(Ind)$_2$HfMe$_2$
B = [C$_6$H$_5$NHMe$_2$][B(C$_6$F$_4$—CC—Si(i-Pr)$_3$)$_4$]
C = [C$_6$H$_5$NHMe$_2$][B(C$_6$F$_5$)$_4$]

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

What is claimed is:

1. A composition of matter comprising a Group-13 atom connected to four aryl ligands wherein at least one aryl is substituted with an acetylene group.

2. The composition of matter of claim 1 wherein at least one aryl ligand is selected from phenyl, indenyl, naphthyl, fluorenyl, or pyrenyl.

3. The composition of matter of claim 2 wherein all of the aryl ligands are the same.

4. The composition of matter of claim 1, wherein the Group-13 atom is boron.

5. The composition of matter of claim 1 wherein the acetylene moiety is substituted with an alkyne functional group connected to a bulky ligand.

6. The composition of matter of claim 1 wherein the acetylene moiety is represented by the following structure:

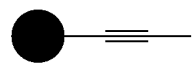

wherein the filled circle represents a bulky group.

7. The composition of matter of claim 1 wherein the acetylene moiety is following formula:

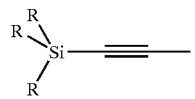

wherein
(a) R are the same or different organic radicals; and
Si is silicon.

8. The composition of matter of claim 7 wherein R is selected from substituted or unsubstituted propyl, isopropyl, butyl, isobutyl, tertiary butyl, pentyl, isopentyl, and cyclohexyl.

9. The composition of matter of claim 1 wherein at least one acetylene moiety is a triisopropylsilyl radical.

10. The composition of matter of claim 1 further comprising a cation.

11. An activator comprising the composition of matter of claim 10 wherein the cation is an activating cation.

12. The activator of claim 11 wherein the cation is one of anilinium, ammonium, trityl carbenium, Group-11 metal, silylium, hydrated Group-1 or -2 metal salt cations.

13. A composition of matter comprising a Group-13 atom connected to three aryl ligands wherein
    (a) at least one aryl ligand is substituted with at least one fluorine atom connected to a ring carbon atom and
    (b) at least one aryl ligand is substituted with an acetylene moiety.

14. The composition of matter of claim 13 wherein at least one aryl ligand is selected from phenyl, indenyl, naphthyl, fluorenyl, or pyrenyl.

15. The composition of matter of claim 14 wherein all of the aryl ligands are the same.

16. The composition of matter of claim 13 wherein the Group-13 atom is boron.

17. The composition of matter of claim 13 wherein the acetylene moiety is substituted with an alkyne functional group connected to a bulky ligand.

18. The composition of matter of claim 13 wherein the acetylene moiety is represented by the following structure:

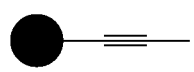

wherein the filled circle represents a bulky group.

19. The composition of matter of claim 13 wherein the acetylene moiety is represented by the following formula:

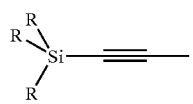

wherein
(a) R are the same or different organic radicals; and
(b) Si is silicon.

20. The composition of matter of claim 18 wherein R is selected from substituted or unsubstituted propyl, isopropyl, butyl, isobutyl, tertiary butyl, pentyl, isopentyl, and cyclohexyl.

21. The composition of claim 13 wherein at least one acetylenic moiety is a triisopropylsilyl radical.

22. A catalyst system comprising the composition of claim 13 and a transition metal catalyst precursor.

23. An olefin polymerization process comprising:
(a) contacting a composition comprising a Group-13 atom connected to four aryl ligands wherein at least one aryl is substituted with an acetylene group with at least one catalyst precursor(s) thereby forming activated catalyst(s) and non-coordinating anion(s); and
(b) contacting the activated catalyst(s) with olefin monomer(s) thereby causing olefin polymerization.

24. A composition represented by one of the following:

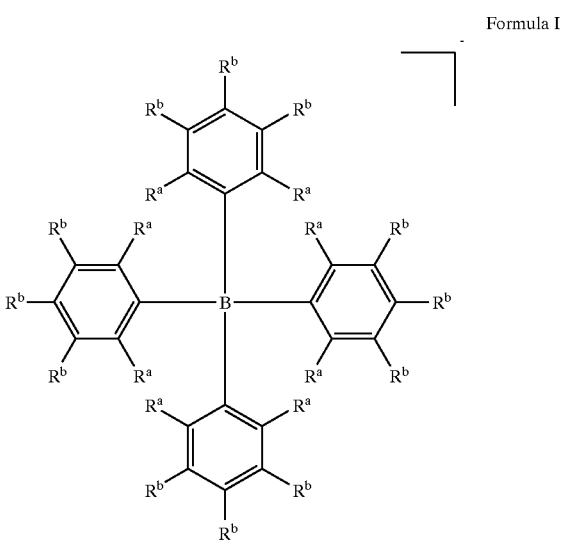

Formula I

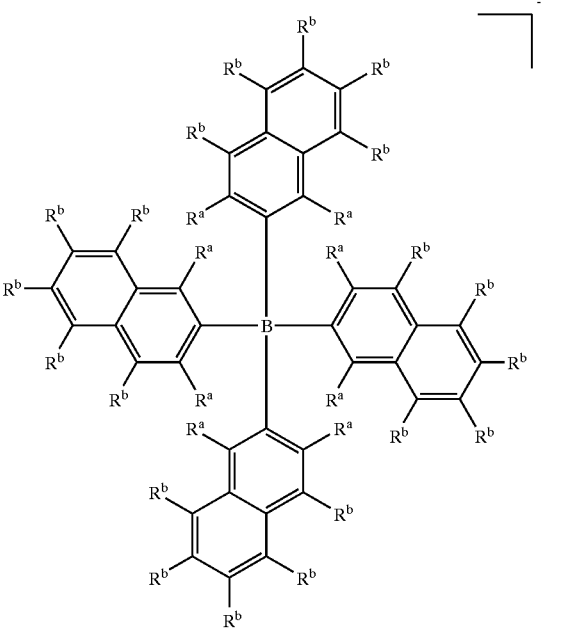

Formula II

Formula III

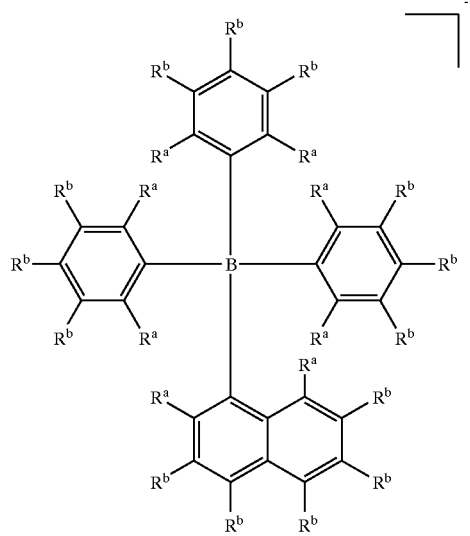

Formula IV

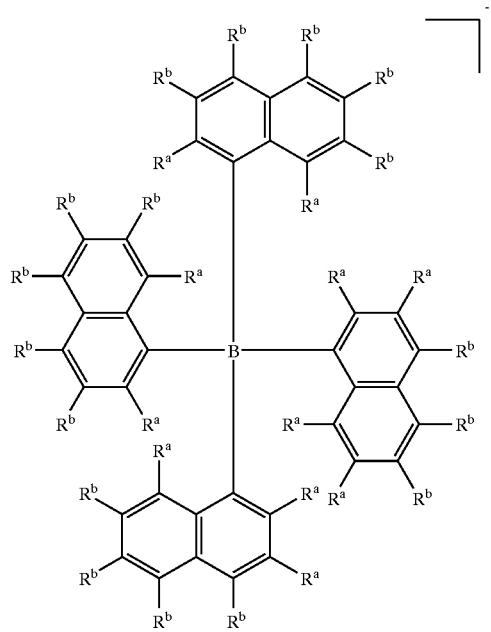

wherein (a) $R^a$ and $R^b$ are independently selected from hydrogen, $C_1$–$C_{30}$ hydrocarbyls, fluorine, or

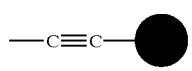

wherein the filled circle represents a bulky group and wherein R are the same or different organic radicals, provided that at least one of $R^a$ or $R^b$ is selected from

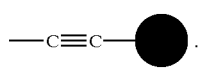.

25. The composition of claim 24 wherein (a) at least one $R^b$ is

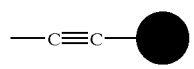

wherein the filled circle represents a bulky group and the remaining $R^b$ are independently selected from from hydrogen, $C_1$–$C_{30}$ hydrocarbyls, fluorine, or

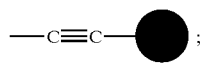;

and (b) $R^a$ are independently selected from hydrogen, $C_1$–$C_{30}$ hydrocarbyls, or fluorine.

26. The composition of claim 24 wherein (a) for each aryl ligand at least one $R^b$ is

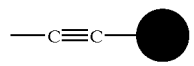

and the remaining $R^b$ are independently selected from from hydrogen, $C_1$–$C_{30}$ hydrocarbyls, fluorine, or

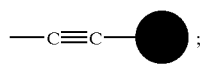;

and (b) $R^a$ are independently selected from hydrogen, $C_1$–$C_{30}$ hydrocarbyls, or fluorine.

27. The composition of claim 24 wherein all aryl ligands are the same.

28. A composition having the following formula:

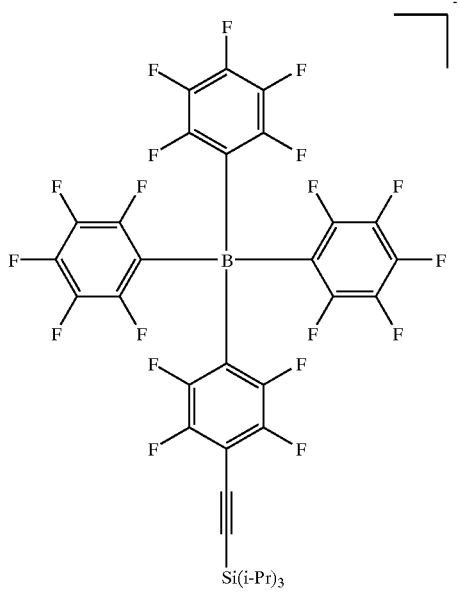

where iPr is isopropyl.

29. A composition having the following formula:

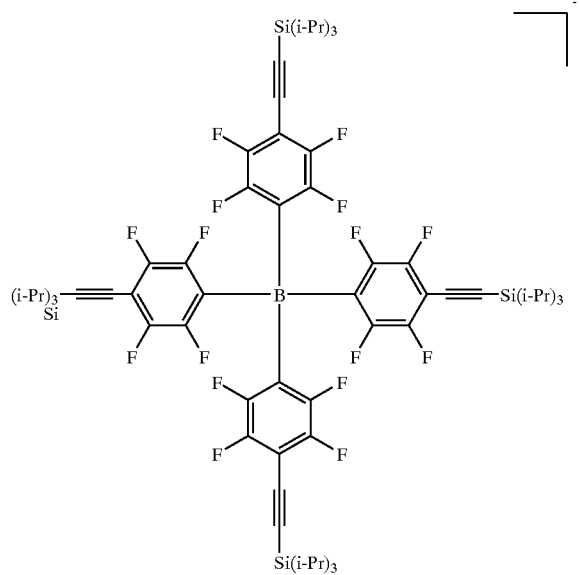

where iPr is isopropyl.

30. A composition represented by one of the following:

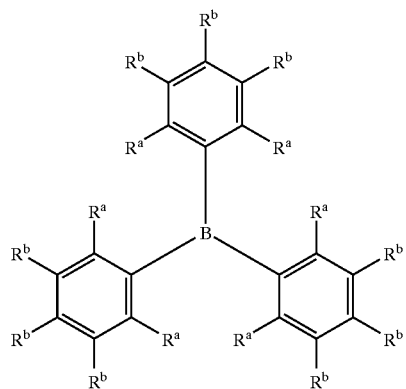

Formula XI

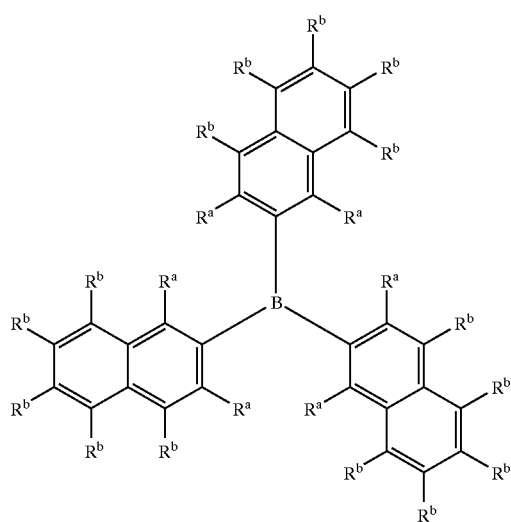

Formula XII

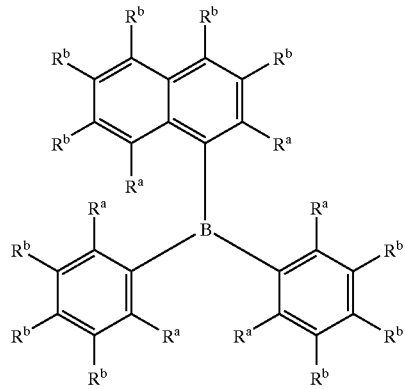

Formula XII

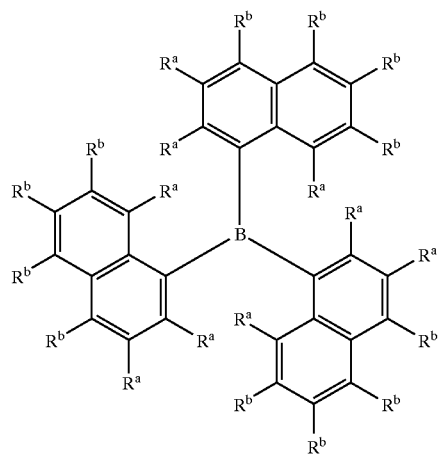

Formula XIV wherein (a) $R^a$ and $R^b$ are independently selected from hydrogen, $C_1$–$C_{30}$ hydrocarbyls, fluorine, or

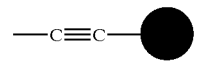

wherein the filled circle represents a bulky group and R are the same or different organic radicals, provided that at least one of $R^a$ or $R^b$ is selected from

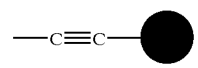

and provided that one of the remaining $R^a$ or $R^b$ is fluorine or a fluorine-substituted hydrocarbyl.

31. The composition of claim 30 wherein (a) at least one $R^b$ is

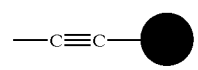

and the remaining $R^b$ are independently selected from from hydrogen, $C_1$–$C_{30}$ hydrocarbyls, fluorine, or —C≡C—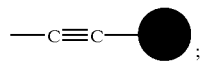;

and (b) $R^a$ are independently selected from hydrogen, $C_1$–$C_{30}$ hydrocarbyls, or fluorine.

32. The composition of claim 30 wherein
(a) for each aryl ligand at least one $R^b$ is —C≡C—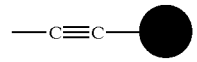

and the remaining $R^b$ are independently selected from from hydrogen, $C_1$–$C_{30}$ hydrocarbyls, fluorine, or —C≡C—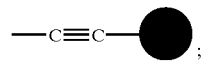;

and (b) $R^a$ are independently selected from hydrogen, $C_1$–$C_{30}$ hydrocarbyls, or fluorine.

33. The composition of claim 30 wherein all aryl ligands are the same.

* * * * *